US005871997A

United States Patent [19]
Rother et al.

[11] Patent Number: 5,871,997
[45] Date of Patent: Feb. 16, 1999

[54] METHODS AND COMPOSITIONS FOR PROTECTING RETROVIRAL VECTOR PARTICLES AND PRODUCER CELLS FROM INACTIVATION BY COMPLEMENT VIA REDUCTION OF THE EXPRESSION OR RECOGNITION OF GALACTOSE ALPHA (1, 3) GALACTOSYL EPITOPES

[75] Inventors: Russell P. Rother, Cheshire; Scott A. Rollins, Monroe; William L. Fodor, New Haven; Jeremy P. Springhorn, Cheshire; Stephen P. Squinto, Bethany, all of Conn.

[73] Assignee: Alexion Pharmaceuticals, Inc., New Haven, Conn.

[21] Appl. No.: 399,416

[22] Filed: Mar. 6, 1995

Related U.S. Application Data

[63] Continuation-in-part of Ser. No. 278,639, Jul. 27, 1994, abandoned.

[51] Int. Cl.[6] .............................. C12N 7/00; C12N 7/06; C12N 7/02; C12N 5/00
[52] U.S. Cl. ...................... 435/235.1; 435/238; 435/239; 435/325
[58] Field of Search ................................. 435/69.1, 20.1, 435/172.3, 235.1; 530/402, 403

[56] References Cited

PUBLICATIONS

Leiden, 1995 New Engl. J. Med. 333:871–873.
Mulligan, 1993 Science 260:926–932.
Brenner, 1994 Immunomethods 5:204–210.
Banapour et al., "The AIDS–Associated Retrovirus is Not Sensitive to Lysis or Inactivation by Human Serum" *Virology*, 152:268–271, 1986.
Barbacid et al., "Humans Have Antibodies Capable of Recognizing Oncoviral Glycoproteins: Demonstration that these Antibodies are Formed in Response to Cellular Modification of Glycoproteins Rather than as Consequence of Exposure to Virus" Proc. Natl. Acad. Sci. USA, 77(3):1617–21, 1980.
Bartholomew et al., "Lysis of oncornaviruses by human serum" *J Exp Med*, 147:844–853, 1978.
Bartholomew and Esser, "Mechanism of antibody–independent activation of the first component of complement (C1) on retrovirus membranes" *Biochem*, 19:2847–2853, 1980.
Cooper et al., "Lysis of RNA tumor viruses by human serum: Direct antibody–independent triggering of the classical complement pathway" *J Exp Med*, 144:970–984, 1976.
Cooper et al., "Genetically Engineered Pigs" *Lancet*, 342:682–683, 1993.
Cornetta et al., "Amphotropic Murine Leukemia Retrovirus is not an Acute Pathogen for Primates" *Human Gene Therapy*, 1:15–30, 1990.
Culver et al., "In vivo gene transfer with retroviral vector–producer cells for treatment of experimental brain tumors" *Science*, 256:1550–1552, 1992.

Donahue et al., "Helper Virus Induced T Cell Lymphoma in Nonhuman Primates after Retroviral Mediated Gene Transfer" *J Exp Med*, 176:1125–1135, 1992.
Galili et al., "Evolutionary relationship between the natural anti–Gal antibody and the Galα1→3Gal epitope in primates" *Proc Natl Acad Sci, USA*, 84:1369–1373, 1987.
Galili et al., "Man, Apes, and Old World Monkeys Differ from Other Mammals in the Expression of α–Galactosyl Epitopes on Nucleated Cells" *J Biol Chem*, 263:17755–17762, 1988.
Galili et al., "Gene Sequences Suggest Inactivation of α–1, 3–Galactosyltransferase in Catarrhines after the Divergence of Apes from Monkeys" *Proc Natl Acad Sci, USA*, 88:7401–7404, 1991, Apr. 30, 1998.
Galili et al., "Evolution and Pathophysiology of the Human Natural Anti–α–galactosyl IgG (Anti–Gal) Antibody" *Springer Semin Immunopathol*, 15:155–171, 1993.
Geyer et al., "Major Oligosaccharides in the Glycoprotein of Friend Murine Leukemia Virus: Structure Elucidation by One– and Two–Dimensional Proton Nuclear Magnetic Resonance and Methylation Analysis" *Biochemistry*, 23:5628–5637, 1984, Apr. 30, 1998.
Hamadeh et al., "Human Natural Anti–Gal IgG Regulates Alternative Complement Pathway Activation on Bacterial Surfaces" *J Clin Invest*, 89:1223–1235, 1992.
Hoshino et al., "Human T–Cell Leukaemia Virus is not Lysed by Human Serum" *Nature*, 310:324–325, 1984.
Isaacs et al., "Vaccinia virus complement–control protein prevents antibody–dependent complement–enhanced neutralization of infectivity and contributes to virulence" *Proc Natl Acad Sci, USA*, 89:628–632, (1992).
Joziasse et al., "Bovine α1→3–Galactosyltransferase: Isolation and Characterization of a cDNA Clone" *J Biol Chem*, 264:14290–14297, 1989.
Kohn et al., "Retroviral–Mediated Gene Transfer into Mammalian Cells" *Blood Cells*, 13:285–298, 1987.
Larsen et al., "Molecular Cloning, Sequence, and Expression of a Human GDP–L–fucose:β–D–galactoside 2–α–L–fucosyltransferase cDNA that Can Form the H Blood Group Antigen" *Proc Natl Acad Sci, USA*, 87:6674–6678, 1990.

(List continued on next page.)

*Primary Examiner*—Donald E. Adams
*Assistant Examiner*—Jeffrey S. Parkin
*Attorney, Agent, or Firm*—Seth A. Fidel

[57] ABSTRACT

Methods and compositions are provided for facilitating gene therapy procedures involving the transduction of target cells with retroviral vector particles in the presence of complement containing body fluids. The reduction of levels of galactose alpha (1,3) galactosyl epitopes on the retroviral vector particles and/or the blockade of antibody binding to such epitopes have been found to render the particles less sensitive to inactivation by complement mediated mechanisms, and to thus allow transduction in the presence of complement containing body fluids. Means are provided for obtaining such reductions.

11 Claims, 19 Drawing Sheets

OTHER PUBLICATIONS

Lowe, "Molecular Cloning, Expression, and Uses of Mammalian Glycosyltransferases" *Semin Cell Biol*, 2:289–307, 1991.

Löwer et al., "Heterophil Human Antibodies Recognize Oncovirus Envelope Antigens: Epidemiological Parameters and Immunological Specificity of the Reaction" *Virology*, 109:409–417, 1981.

McNearney et al., "Herpes simplex virus glycoproteins gC–1 and gC–2 bind to the third component of complement and provide protection against complement–mediated neutralization of viral infectivity" *J Exp Med*, 166:1525–1535, 1987.

Martinez et al., "Partial Reconstitution of Replication–Competent Retrovirus in Helper Cells with Partial Overlaps Between Vector and Helper Cell Genomes" *Human Gene Therapy*, 7:705–712, 1996.

Neethling et al., "Protection of pig kidney (PK15) cells from the cytotoxin effect of anti–pig antibodies by α–galactosyl oligosaccharides" *Transplantation*, 57:959–963, 1994.

Ram et al., "Toxicity studies of retroviral–mediated gene transfer for the treatment of brain tumors " *J Neurosurg*, 79:400–407, 1993.

Repik et al., "Differential host–dependent expression of α–galactosyl epitopes on viral glycoproteins: a study of eastern equine encephalitis virus as a model" *J Gen Virol*, 75:1177–1181, 1994.

Rother et al., "Inhibition of complement–mediated cytolysis by the terminal complement inhibitor of herpesvirus saimiri" *J Virol*, 68:730–737, 1994.

Rother et al., "Protection of Retroviral Vector Particles in Human Blood through Complement Inhibition" *Human Gene Therapy*, 6:429–435, 1995.

Rother et al., "A Novel Mechanism of Retrovirus Inactivation in Human Serum Mediated by Anti–α–Galactosyl Natural Antibody" *J Exp Med*, 182:1345–1355, 1995.

Sandrin et al., "Biochemical Features of Pig to Human Xenografts" *J Leukocyte Biol*, O (Suppl.) :66, 1993.

Sandrin et al., "Anti–Pig IgM Antibodies in Human Serum React Predominantly with Gal (α1–3)Gal Epitopes" *Proc Natl Acad Sci, USA*, 90:11391–11395, 1993.

Sandrin et al., "Gal α(1–3) Gal, the Major Xenoantigen(s) Recognized in Pigs by Human Natural Antibodies" *Immunol Reviews*, 141:160–190, 1994.

Sherwin et al., "Complement–Mediated Lysis of Type–C Virus: Effect of Primate and Human Sera on Various Retroviruses" *Int J Cancer*, 21:6–11, 1978.

Snyder et al., "Specificity of Human Antibodies to Oncovirus Glycoprotiens: Recognition of Antigen by Natural Antibodies against Carbohydrate Structures" *Proc Natl Acad Sci, USA*, 77:1622–1626, 1980.

Spear et al., "Direct Binding of Complement Component C1q to Human Immunodeficiency Virus (HIV) and Human T Lymphotrophic Virus–I (HTLV–!) Coinfected Cells" *AIDS Research Human Retroviruses*, 7:579–585. 1991.

Takeuchi et al., "Type C Retrovirus Inactivation by Human Complement Is Determined by both the Viral Genome and the Producer Cell" *J Virol*, 68:8001–8007, 1994.

Thall et al., "Distribution of Galα1→3Galβ1→4GlcNAc Residues on Secreted Mammalian Glycoproteins (Thyroglobulin, Fibrinogen, and Immunoglobulin G) as Measured by a Sensitive Solid–Phase Radioimmunoassay" *Biochemistry*, 29:3959–3965, 1990.

Thiry et al., "Factors which Influence Inactivation of Vesicular Stomatitis Virus by Fresh Human Serum" *Virology*, 87:384–393, 1978.

Vaughn et al., "Biochemical Analysis of Pig Xenoantigens Detected by Human Antibodies" *Transplantation Proc*, 25:2919–2920, 1993.

Welsh et al., "Human serum lyses RNA tumour viruses" *Nature*, 257:612–614, 1975.

Welsh et al., "Inactivation and lysis of oncornaviruses by human serum" *Virology*, 74:432–440, 1976.

Widner and Brundin, "Immunological aspects of grafting in the mammalian central nervous system. A review and speculative synthesis" *Brain Res Rev*, 13:287–324, 1988.

METHODS AND COMPOSITIONS FOR PROTECTING RETROVIRAL VECTOR PARTICLES AND PRODUCER CELLS FROM INACTIVATION BY COMPLEMENT VIA REDUCTION OF THE EXPRESSION OR RECOGNITION OF GALACTOSE ALPHA (1, 3) GALACTOSYL EPITOPES

CROSS-REFERENCE TO RELATED APPLICATIONS

This is a continuation-in-part of U.S. Ser. No. 08/278,639, filed Jul. 27, 1994, now abandoned, in the names of Russell P. Rother, Scott A. Rollins, William L. Fodor, and Stephen P. Squinto, and entitled "Retroviral Transduction of Cells in the Presence of Complement."

FIELD OF THE INVENTION

The present invention relates to gene therapy mediated by the transduction of primate cells by retroviral vector particles (RVVPs) and, in particular, to methods and compositions for modulating the recognition of the RVVPs by the humoral immune system as well as modulation of complement activity to allow the medical use of such particles for transduction of human and other primate cells without removing the cells from contact with the extracellular fluids of the host organism.

BACKGROUND OF THE INVENTION

I. Retroviruses

The Retroviridae virus family encompasses all viruses containing an RNA genome and producing an RNA-dependent DNA polymerase (reverse transcriptase). In broadest overview, the life cycle of a retrovirus comprises entry of an infectious retroviral particle into a host cell, integration of the virus' genetic information into the host cell's genome, and production of new infectious retroviral particles by the biosynthetic machinery of the infected host cell. More specifically, upon entering a cell, a retroviral particle initiates a series of interactive biochemical steps that result in the production of a DNA copy of the virus' RNA genome and its integration into the nuclear DNA of the cell. This integrated DNA copy is referred to as a provirus and can be inherited by any daughter cells of the infected cell like any other gene. Genes contained within the integrated provirus may be expressed in the host cell.

All retroviral particles share common morphological, biochemical, and physical properties, including:

(1) A linear, positive-sense, single-stranded RNA genome composed of two identical subunits and making up about 1% of the mass of the virus.
(2) At least three types of proteins encoded by the viral genome, i.e., gag proteins (the group antigen internal structural proteins), pol proteins (the RNA-dependent DNA polymerase and integrase proteins), and env proteins (the viral envelope protein or proteins). These proteins together make up about 60%–70% of the mass of the virus.
(3) Lipid derived from the cell membrane of an infected cell making up about 30%–40% of the mass of the virus.
(4) Carbohydrate associated with the env proteins, making up about 2–4% of the mass of the virus.
(5) An overall spherical morphology with variable surface projections.
(6) An isocahedral capsid structure containing a ribonucleoprotein complex within an internal nucleoid or nucleocapsid shell.

In addition to genes encoding the gag, pol, and env proteins, the genome of the retrovirus includes two long terminal repeat (LTR) sequences, one at each end of the linear genome. These 5' and 3' LTRs serve to promote transcription and polyadenylation of viral mRNAs. Adjacent to the 5' LTR are sequences necessary for reverse transcription of the viral genome (the tRNA primer binding site) and for efficient encapsulation of viral RNA into particles (the Psi site). Other genes may also be found between the 5' and 3' LTRs of the retroviral genome.

If heterologous genes are inserted in between the 5' and 3' LTRs of a retroviral genome, which is then packaged into a functional retroviral particle, the resulting recombinant retroviral particle is capable of carrying the heterologous genes into a host cell. Upon integration of the recombinant retroviral genome into the host cell's genome as part of the proviral DNA, the heterologous genes may be expressed.

These properties and capabilities have led to the development of retroviral vectors, retroviral packaging and producer cells, which are typically prepared from cells of murine origin, and retroviral vector particles (collectively referred to as retroviral transduction systems) as efficient means of stably introducing exogenous genes of interest into mammalian cells. Certain retroviruses have been engineered to produce non-infectious retroviral transduction systems that are especially useful in the field of gene therapy. See, for example, Anderson, 1992; Miller, 1992; Mulligan, 1983; Mann, 1983; Cone and Mulligan, 1984.

II. Gene Transfer by Retroviral Transduction

Retroviral transduction systems of the type discussed above are able to introduce recombinant nucleic acid molecules into mammalian target cells, and to efficiently integrate DNA molecules containing some or all of the genetic information (sequence) of the introduced recombinant nucleic acid molecule into the genome of the target cell so that the introduced genetic material is replicated and is stably and functionally maintained (and any encoded gene products are expressed) in the cell without the danger of the production of replicating infectious virus. See, for example, Ausubel, et al., Volume 1, Section III (units 9.10.1–9.14.3), 1992.

Retroviral vector particles are particularly useful for genetically modifying mammalian cells, including human cells, because the efficiency with which they can transduce target cells and integrate their genetic information into the target cell genome is higher than that achievable using other systems of introducing exogenous genetic material into cells. Other advantages associated with the use of retroviral vector particles as gene therapy agents include stable expression of transferred genes, capacity to transfer large genes, and lack of cellular cytotoxicity. Additionally, retroviral vector articles may be constructed so as to be capable of transducing mammalian cells from a wide variety of species and tissues.

Successful gene transfer by transduction with a retroviral vector particle (RVVP) requires: 1) incorporation of a gene of interest into a retroviral vector; 2) packaging of a vector-derived viral genome into a RVVP; 3) binding of the RVVP to the target cell; 4) penetration of at least the RNA molecules comprising the viral genome into the target cell (generally associated with penetration of the RVVP and uncoating of the RVVP); 5) reverse transcription of the viral RNA into pre-proviral cDNA; 6) incorporation of the pre-proviral cDNA into preintegration complexes, 7) translocation of the preintegration complexes into the target cell nucleus, 8) generation of stable proviral DNA by integration of the pre-proviral cDNA into the host genome (typically mediated by the viral integrase protein); and 9) expression of the gene of interest. In the in vivo setting (and in some ex vivo settings), the RVVP must survive in the extracellular fluids of the host organism in an active state for a period sufficient to allow binding and penetration of the host target cell by the RVVP.

Gene Therapy: There is active research, including clinical trial research, on treatment of disease by introduction of genetic material into some of the cells of a patient. A variety of diseases may be treated by therapeutic approaches that involve stably introducing a gene into a cell such that the gene may be transcribed and the gene product may be produced in the cell. Diseases amenable to treatment by this approach include inherited diseases, particularly those diseases that are caused by a single gene defect. Many other types of diseases, including acquired diseases, may also be amenable to gene therapy. Examples of such acquired diseases include many forms of cancer, lung disease, liver disease, and blood cell disorders. See Anderson, 1992; Miller, 1992; and Mulligan, 1993.

Delivery of the gene or genetic material into the cell is the first critical step in gene therapy treatment of disease. A variety of methods have been used experimentally to deliver genetic material into cells. Most research has focused on the use of retroviral and adenoviral vectors for gene delivery. As discussed above, RVVPs are particularly attractive because they have the ability to stably integrate transferred gene sequences into the chromosomal DNA of the target cell and are very efficient in stably transducing a high percentage of target cells. Accordingly most clinical protocols for gene therapy use retroviral vectors (see, for example, Miller, 1992; and Anderson, 1992).

Most gene therapy protocols involve treating target cells from the patient ex vivo and then reintroducing the cells into the patient. Patients suffering from several inherited diseases that are each caused by a single gene defect have already received gene therapy treatments. Such treatments generally involve the transduction of the patient's cells in vitro using RVVPs designed to direct the expression of therapeutic molecules, followed by reintroduction of the transduced cells into the patient. In many cases such treatments have provided beneficial therapeutic effects.

For many diseases, however, it will be necessary to introduce the gene into the target cell in situ, because the target cells cannot be removed from and returned to the body. In other cases, cells that are removed from the patient must be maintained in the presence of body fluids until being returned to the body. Stem cells, particularly hematopoietic stem cells, are an especially important type of target cell for gene therapy of inheritable and acquired blood disorders. Such cells are intrinsically unstable in vitro, and tend to differentiate into cells that are less attractive targets for gene therapy, especially when they have been washed free of the fluids that surround them in vivo and transferred into body-fluid-free tissue culture media or the like.

Accordingly, it is desirable to transduce stem cells as quickly as possible, and ex vivo treatment of such cells with RVVPs is best carried out in the cells natural milieu, i.e., in cells that have not been washed or otherwise removed from the body fluids in which they are obtained, e.g., hematopoietic stem cells in bone marrow aspirates. In the case of stem cells in bone marrow, current medical procedures for bone marrow transplant involve mixing an ex vivo bone marrow aspirate (which is inevitably obtained as a mixture of bone marrow and blood) with an anticoagulant, typically heparin, and tissue culture medium. The condition of such cells, that have been removed from the body but kept in diluted or undiluted fluids of their natural milieu, is referred to hereinafter as the "ex vivo unwashed state".

III. The Humoral Immune System and Retroviral Vector Particles

A longstanding problem associated with the use of RVVPs as gene therapy vectors in cells in vivo or in cells in the ex vivo unwashed state relates to the inactivation of many retroviruses (and RVVPs derived therefrom) by the body fluids (e.g., blood, bone marrow, lymph) of many primates, including Old World monkeys, apes, and humans. Indeed, it has been known for almost two decades that certain retroviruses are rapidly inactivated in human serum (Welsh et al., 1975), as well as serum from nonhuman primates (Welsh et al., 1976). This problem has precluded the use of such RVVPs for gene therapy in vivo or in the ex vivo unwashed state.

The humoral immune system, and particularly the complement system has long been implicated in the serum mediated inactivation of retroviruses, as serum deficient in C2, C4 or C8 does not cause the detectable release of reverse transcriptase from retroviral virions (Welsh et al., 1975; Cooper, et al., 1976). The protection of active retroviral particles from human complement is thus necessary for the use of the RVVPs to mediate gene therapy in human cells in vivo or in the ex vivo unwashed state. Accordingly, to date, gene transfer by retroviral transduction has been, for the most part, limited to cells that were removed from the extracellular fluids of the host organism (i.e., ex vivo cells that are not in the ex vivo unwashed state) and thus were not subjected to complement attack. This limitation has represented a significant shortcoming of this technology.

The need for methods allowing transduction of primate cells in situ, in vivo, or in the ex vivo unwashed state has resulted in the development of methods designed to prevent the inactivation of retroviruses by human and other primate sera. Such methods have included the removal of cells from the extracellular fluids of the host organism, as discussed above, as well as the masking of virion structures that can activate complement activity by administration of isolated C1s and/or C1q complement subcomponents, as discussed below under the subheading "The Direct C1 Binding Mechanism".

Significantly, with regard to the present invention, no previous methods for allowing transduction of primate cells in situ, in vivo, or in the ex vivo unwashed state have included methods or compositions for preventing antibody binding to alpha galacotsyl epitopes on virion cell surface molecules.

The Direct C1 Binding Mechanism: Retroviruses that are sensitive to human serum have been reported to activate the human classical complement pathway by a mechanism that involves an antibody independent process. This process is found in many primates and is generally not present in other mammals (see Cooper, et al., 1976). This mechanism is activated when complement component C1 binds to retroviral virions directly and triggers the classical complement pathway, just as the pathway is normally activated by an antigen-antibody complex (Bartholomew, et al., 1978). The complement cascade then causes the eventual destruction and elimination of the virus. Prior to the present invention, it has generally been believed in the art that this mechanism provides the major, if not the only, means by which retroviral virions are destroyed by the humoral immune system.

Complement component C1 is a large complex protein composed of 3 subunits designated C1q, C1s, and C1r. C1q is itself composed of 18 polypeptide chains of three different types designated A, B, and C. Six molecules each of chains A, B, and C compose the C1q subunit. There are two molecules each of the C1s subunit and the C1r subunit that associate with C1q to form the C1 complement component. The C1q subunit contains multiple identical binding sites for the complement binding regions of immunoglobulin molecules, which regions are only exposed upon the formation of an antigen-antibody complex. In the classical pathway, the binding of C1q to these regions of antigen-bound antibody molecules causes a conformational change in the Cl complex resulting in the enzymatic activation of C1 to yield an active serine protease. The C1s and C1q subunits both have a molecular weight of approximately 85 kDa, and each is cleaved to smaller molecular weight forms of approximately 57 kDa and 28 kDa during activation of the C1 complex. The 57 kDa forms of C1s and C1q present in the activated C1 complex contain the protease activity.

In the activation of the classical complement pathway by retroviruses via direct binding of C1, the C1q subunit of Cl binds directly to at least one site on the retroviral virion. In the case of Moloney murine leukemia virus, the p15E viral protein has been identified as the C1 binding receptor. See Bartholomew, et al., 1978. In contrast to the antibody-mediated classical complement pathway, binding by both the C1q subunit and the C1s subunit of the Cl complex is required for complement activation by retroviral particles via this mechanism. Furthermore, the C1s subunit and C1q subunit must bind the viral particle when they are present in a functional Cl complex in order for complement activation to occur by this mechanism. See Bartholomew, et al., 1980.

The C1s subunit is also believed to have a specific binding site for retroviral coat proteins. It has been shown, using inactive retrovirus, that pre-binding with C1s blocks the subsequent activation of the complement cascade by the retrovirus in vitro. See Bartholomew, et al., 1980.

Co-pending U.S. patent application Ser. No. 08/098,944 ("the '944 application"), filed Jul. 28, 1993 in the name of James M. Mason and entitled "Pre-binding of Retroviral Vector Particles with Complement Components to Enable The Performance of Human Gene Therapy In Vivo," discuses the use of free C1q or free C1s to block the subsequent binding and/or activation of the C1 complex by active retrovirus particles including RVVPs.

As described therein, C1s or C1q or a combination thereof are incubated with the RVVPs in vitro to form complexes with the particles. This complex formation blocks the binding sites for C1s and/or C1q and thereby protects the particles from subsequent inactivation or lysis when the RVVPs are exposed to complement. As further described therein, blockade of intact C1 binding to RVVPs can be achieved by the use of fragments of antibodies that bind the viral envelope proteins of RVVPs but lack complement binding regions.

As disclosed in the '944 application, the use of these methods improves the survival of RVVPs in human serum, but does not completely inhibit retroviral inactivation. The incomplete nature of the inhibition of retroviral inactivation by these methods have heretofore been unexplained.

Many gene therapy methods require very high titers of transducing RVVPs in order to be practiced effectively. The methods of the '944 application are of limited efficacy, as they do not provide a sizable inhibition of complement mediated RVVP inactivation, and thus may not provide high enough titers of RVVPs in vivo or in the ex vivo unwashed state for the effective practice of all such gene therapy methods.

Thus, a need continues to exist for methods to control complement-mediated destruction of RVVPs. The present invention provides new methods and compositions that can be used in conjunction with, or as an alternative to other methods of protecting RVVPs from inactivation by complement such as the blockade of intact C1 binding to RVVPs as disclosed in the '944 application. The methods and compositions of the present invention thus allow the practice of more efficient gene therapy procedures in vivo, in situ, and in the ex vivo unwashed state.

IV. The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins (which are also found in most other body fluids, such as lymph, bone marrow, and cerebrospinal fluid) make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade progresses via the classical pathway or the alternative pathway. These pathways share many components, and, while they differ in their early steps, both converge and share the same terminal complement components responsible for the damage and destruction of target cells and viruses.

The classical complement pathway is typically initiated by antibody recognition of and binding to an antigenic site on a target cell. This surface bound antibody subsequently reacts with the first component of complement, C1, which, as discussed above, includes subunits C1s, C1r, and C1q.

The C1q subunit of C1 mediates the binding of C1 both to antigen-antibody complexes and to retroviruses, although, in the case of direct binding to retroviruses, the C1s subunit also has a binding function. The bound C1 undergoes a set of autocatalytic reactions that result in the activation of the C1r subunits, which in turn proteolytically activate the C1s subunits, altering the conformation of C1 so that the active C1s subunits are exposed on the exterior of C1, where they can interact proteolytically with complement components C2 and C4.

C1s cleaves C2 and C4 into C2a, C2b, C4a, and C4b. The function of C2b is poorly understood. C2a and C4b combine to form the C4b,2a complex, which is an active protease known as the C3 convertase. C4b,2a acts to cleave C3 into C3a and C3b. C3a is a relatively weak anaphylatoxin. C4a is a stronger anaphylatoxin, and can induce degranulation of mast cells, resulting in the release of histamine and other mediators of inflammation.

C3b has multiple functions. As opsonin, it binds to bacteria, viruses and other cells and particles and tags them for removal from the circulation. C3b can also form a complex with C4b,C2a to produce C4b,2a,3b, or C5 convertase, which cleaves C5 into C5a (another anaphylatoxin), and C5b. C5b combines with C6 yielding C5b,6, and this complex combines with C7 to form the ternary complex C5b,6,7. The C5b,6,7 complex binds C8 at the surface of a cell membrane. Upon binding of C9, the complete membrane attack complex (MAC) is formed (C5b-9) which mediates the damage and lysis of foreign cells, microorganisms, and viruses.

A more complete discussion of the classical complement pathway, as well as a detailed description of the alternative pathway of complement activation, which pathway has also been implicated in the inactivation of RVVPs by human complement, can be found in Roitt, et al., 1988.

V. Galactose Alpha (1,3) Galactosyl Epitopes

Natural human antibodies are preformed antibodies that bind to epitopes of foreign antigens (xenoepitopes). Several recent studies have convincingly demonstrated that the galactose alpha (1,3) galactosyl carbohydrate epitopes, also referred to as Gal α(1,3) Gal epitopes, are major xenoepitopes recognized by natural human antibodies (see Sandrin, et al., 1993A; Sandrin, et al., 1993B; copending U.S. patent application Ser. No. 08/214,580, entitled "Xenotransplantation Therapies", filed by Mauro S. Sandrin and Ian F. C. McKenzie on Mar. 15, 1994; copending U.S. patent application Ser. No. 08/278,282, entitled "Methods for Reducing Hyperacute Rejection of Xenografts", filed Jul. 21, 1994 in the names of Mauro S. Sandrin, William L. Fodor, Russell P. Rother, Stephen P. Squinto, and Ian F. C. McKenzie; and PCT publication No. 93/03735, entitled "Methods and Compositions for Attenuating Antibody-Mediated Xenograft Rejection"). In addition, it has been suggested that galactose alpha (1,3) galactosyl epitopes on certain DNA viruses may be involved in triggering immune responses (Repik et al., 1994).

Galili and colleagues have shown that a large proportion of IgG (1%) in human serum is directed against the galactose alpha (1,3) galactosyl epitopes expressed as part of a variety of glycosylated molecules found on both cell surfaces and on secreted glycoproteins (Galili et al., 1984; and Thall and Galili, 1990). This disaccharide epitope is found in all mammals except humans and Old World primates, and naturally occurring preformed anti-α(galactosyl antibodies e.g., anti-galactose alpha (1,3) galactose antibodies—i.e., antibodies that bind specifically to galactose alpha (1,3) galactosyl epitopes—are found only in humans and Old World primates, i.e., those species that do not themselves express the epitope (Galili et al., 1987 and Galili et al., 1988).

The ability of different monosaccharides and oligosaccharides to inhibit the interaction of naturally occurring preformed human antibodies with pig cells and to prevent the antibody-dependent and complement-mediated damage and lysis of pig cells has been examined (Sandrin et al., 1993A; Sandrin et al., 1993B; PCT publication No. 93/03735, supra; and copending U.S. patent application Ser. No. 08/214,580, supra).

Inhibition of the binding of such antibodies to xenogeneic cells was obtained with galactose, or with moieties containing terminal galactose in an alpha linkage but not a beta linkage. Various carbohydrates have also been shown to contain the target epitopes for several types of naturally occurring preformed human antibodies with other specificities (e.g., ABO blood group antibodies). However, no monosaccharide tested, other than those containing the galactose alpha (1,3) galatosyl epitope, had any inhibitory effect on the binding of naturally occurring preformed human antibodies to xenogeneic cells. Identical inhibition results were obtained when individual human serum samples from blood group A, B, AB or O individuals were used (Sandrin et al., 1993A and Sandrin et al., 1993B).

Similarly, Cooper and colleagues have demonstrated that, of a total of 132 carbohydrates screened for binding to preformed naturally occurring human IgG and IgM antibodies, each of the four carbohydrate molecules that they found could bind such antibodies contained a terminal alpha galactose (Good et al., 1992). The four carbohydrates were:
(1) Gal α(1,3) Gal β(1,4) GlcNAc,
(2) Gal α(1,3) Gal β(1,4) Glc,
(3) Gal α(1,3) Gal β, and
(4) Gal α(1,3) Gal.

Sugars such as melibiose (a disaccharide containing a terminal galactose in an alpha (1,3) linkage) coupled to a carrier such as SEPHAROSE can be used to purify anti-galactose alpha (1,3) galactose antibodies (Galili et al, 1984 and Galili et al., 1985). In some antibody absorption experiments, human serum was passed over the carrier-sugar matrix in order to prepare serum from which the antibodies reactive with the sugar were removed. The results of testing the cytolytic activity of the sera prepared in these experiments indicate that the majority of the cytotoxic antibodies were removed from the serum by these means (Sandrin et al., 1993A; Sandrin et al., 1993B).

In sum, the results of the sugar inhibition studies, the studies of the binding of antibodies to galactose alpha (1,3) galatosyl epitope-containing molecules, and the studies of the absorption of antibodies by melibiose-SEPHAROSE, all lead to the conclusion that galactose alpha (1,3) galactosyl epitopes are amongst the most important epitopes detected by naturally occurring human antibodies.

Inhibitors of Glycosylation

Glycosylation of retroviral proteins, including the glycosylated envelope protein (gp70), is a dynamic process involving the host cell translational machinery. Mature glycoproteins which contain asparagine linked (N-linked) oligosaccharides fall generally into three categories, depending on the oligosaccharide side chains of their carbohydrate moieties: high mannose, complex, and hybrid types. These side chain oligosaccharides are added to nascent proteins through a well characterized biosynthetic pathway (for review see Kornfeld and Kornfeld, 1985).

This pathway is initiated with the addition of a glucosylated high mannose oligosaccharide precursor, $(Glc)_3(Man)_9(GlcNAc)_2$. This high mannose precursor is trimmed by various glucosidases and mannosidases as the protein traverses the rough endoplasmic reticulum and golgi apparatus, respectively. When high mannose oligosaccharide side chains are not trimmed by the mannosidases, the high mannose type side chain results. When high mannose oligosaccharide sides chains are trimmed by the mannosidases and are subsequently modified to contain glucosamine, fucosyl, galactosyl, and other side chain additions, the complex type side chain results. Intermediates between these two end products are termed hybrid side chains.

SUMMARY OF THE INVENTION

In view of the foregoing state of the art, it is an object of the present invention to facilitate the use of RVVPs to efficiently transduce the cells of a primate patient, e.g., a human patient, upon administration of the RVVPs to cells in contact with the body fluids of the patient. Since the RVVPs of the invention are generally used to effect gene therapy, such RVVPs preferably contain an exogenous gene operably linked to a promoter effecting the expression of the gene and operably linked to a portion of the vector which recombines with DNA in the genome of the patient.

It is an additional object of the present invention to provide agents and methods that inhibit the inactivation of retroviral vector particles by complement and thus allow the effective administration of transducing retroviral vector particles to host cells in the presence of host body fluids.

It is yet another object of the present invention to provide pharmaceutical agents for gene therapy in primates, and to provide articles of manufacture containing such agents.

In order to achieve these and other objects, the invention provides certain retroviral packaging and producer cells which are less prone to hyperacute rejection when exposed to body fluids such as human blood, plasma, serum, lymph, or the like (e.g., when administered to cells in vivo or in the ex vivo unwashed state) than typical, NIH 3T3 cell-derived retroviral packaging and producer cells. These cells are protected from damage mediated by antibodies in human or Old World primate body fluids that recognize a galactose alpha (1,3) galactosyl epitope.

In accordance with the invention, these cells, the complement resistant RVVPs derived therefrom, and the other protected RVVPs of the invention do not pose the safety hazards associated with human and Old World primate cells and products derived therefrom (e.g., contamination with human pathogens, including viral, prion, or other pathogenic contaminants that are more likely to be found in human or Old World primate cells that in the cells of the invention). The invention also provides methods for the preparation of such cells, and for the preparation of protected RVVPs from such cells.

In accordance with various of these methods, the packaging cells or the producer cells of the invention are derived from non-Old World Primate cells or cell lines that have been modified and/or selected in order to obtain cells that do not express galactose alpha (1,3) galactosyl epitopes. When modifying and/or selecting cells, the modification and/or selection steps may be carried out before, during, or after the introduction of retroviral genes into the cells of such cell lines for the purpose of deriving packaging and producer cells.

One method for preparing such modified cells is discussed in copending U.S. patent application Ser. No. 08/278,282, entitled "Methods for Reducing Hyperacute Rejection of Xenografts", filed Jul. 21, 1994 in the names of Mauro S. Sandrin, William L. Fodor, Russell P. Rother, Stephen P. Squinto, and Ian F. C. McKenzie. Other methods of modifying and/or selecting cell lines are provided by the present invention.

Selection methods include screening of mammalian cells (including cells of cell lines) for cell surface expression of galactose alpha (1,3) galactosyl epitopes. Such screening can be carried out using specific detection agents. Such agents include preparations that contain antibodies that specifically bind to the epitopes (e.g., antibody solutions containing anti-Gal α(1,3) Gal antibodies, such solutions including human serum, which typically contains such antibodies) or preparations that contain lectins or other detection agents specific for the epitopes, such as the IB4 lectin discussed below. Binding of the detection agents to non-permiablized cells indicates that the cells express galactose alpha (1,3) galactosyl epitopes on their cell surfaces. Binding can be detected by various indirect or direct labeling means, including by fluorescence (e.g., by fluorescence microscopy or FACS analysis), by histochemical labels such as enzymes, and by radioactive labels. Such screening is used to identify and select cells that are deficient in the galactose alpha (1,3) galactosyl epitope.

Modification methods include:
1 effecting gene knockouts of the galactose alpha (1,3) galactosyl transferase genes so as to modify parent cells from which the producer cells or packaging cells of the invention are derived;
2 causing the expression of antisense RNA molecules interfering with the expression of galactose alpha (1,3) galactosyl transferase in the parent cells;
3 introducing into the parent cells antisense oligonucleotides interfering with the expression of galactose alpha (1,3) galactosyl transferase in the parent cells;
4 introducing into the parent cells nucleic acid constructs directing the expression of antibody-derived proteins that are retained intracellularly ("intrabodies") that bind specifically to galactose alpha (1,3) galactosyl epitopes, or that bind to and inhibit the activity of galactose alpha (1,3) galactosyl transferase in the parent cells.

The invention also provides inhibitory methods for reducing or preventing the expression of galactose alpha (1,3) galactosyl epitopes by retroviral packaging cells or producer cells. These methods involve growing the cells in the presence of chemical inhibitors of carbohydrate synthesis.

The invention also provides methods for the removal of galactose alpha (1,3) galactose from the RVVPs by incubating the RVVPs in the presence of glycosidases or mannosidases that enzymatically remove this carbohydrate moiety.

In addition to the modulation of the expression of galactose alpha (1,3) galactosyl epitopes by producer or packaging cells, the invention provides methods involving the administration of inhibitory molecules that reduce the binding of antibodies to such epitopes found on producer cells and on retroviral vector particles. In accordance with the invention, such administration results in the inhibition of natural antibody-mediated activation of the complement cascade.

The invention further provides pharmaceutical compositions containing such inhibitor molecules together with producer cells and/or retroviral vector particles. In certain embodiments the pharmaceutical compositions are distributed as articles of manufacture comprising the pharmaceutical compositions of the invention and packaging material comprising a label that indicates that the pharmaceutical compositions are to be used to provide gene therapy treatment to a patient.

The present invention stems from the discovery, disclosed herein, that, contrary to the prior consensus in the art, the antibody-independent direct binding of C1 to retroviral virions is not the only significant cause of the inactivation of retroviral virions by primate body fluids (e.g., blood, plasma, serum, etc.). While not wishing to be bound by any particular theory of operation, it is believed that in human and Old World primate sera, preformed natural antibodies reactive with galactose alpha (1,3) galactosyl epitopes provide an additional mechanism, heretofore unrecognized, by which complement-mediated inactivation of retroviral virions is initiated.

Figure 4:
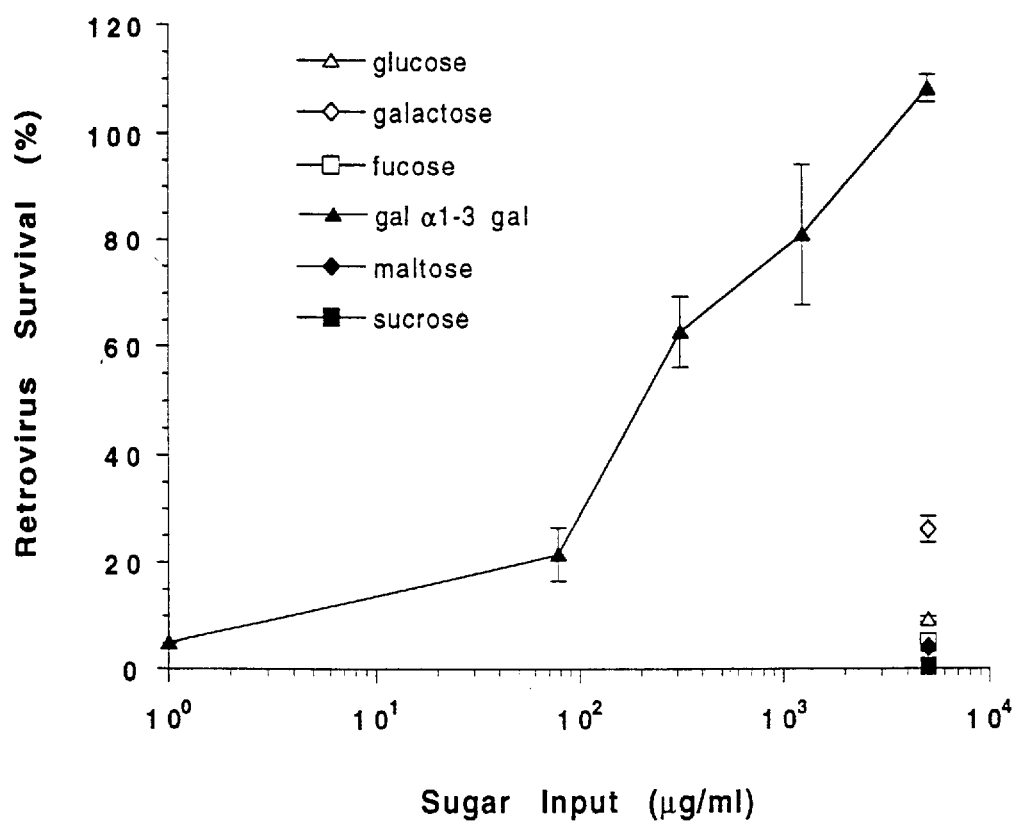

FIG. 4 shows Inhibition of retrovirus inactivation in human serum using soluble Galα1-3Gal. Amphotropic retroviral particles were incubated in 40% human serum in the presence of soluble carbohydrates including D(+) glucose (glucose), D(+) galactose (galactose), α-L(-) fucose (fucose), galactose α1-3 galactose (gal α1-3 gal), maltose or sucrose. Following exposure to serum, the retroviral particles were titered on NIH/3T3 cells to assess survival. The curve represents the percentage of infectious particles remaining at various concentrations of input Gal α1-3 Gal relative to virus survival in 40% heat inactivated human serum. Single points indicate retrovirus survival in the presence of various other carbohydrates at a concentration of 5 mg/ml. Data represent duplicate determinations from a single experiment, one of three so performed. Error bars denote standard error of the mean.

Figure 5A:
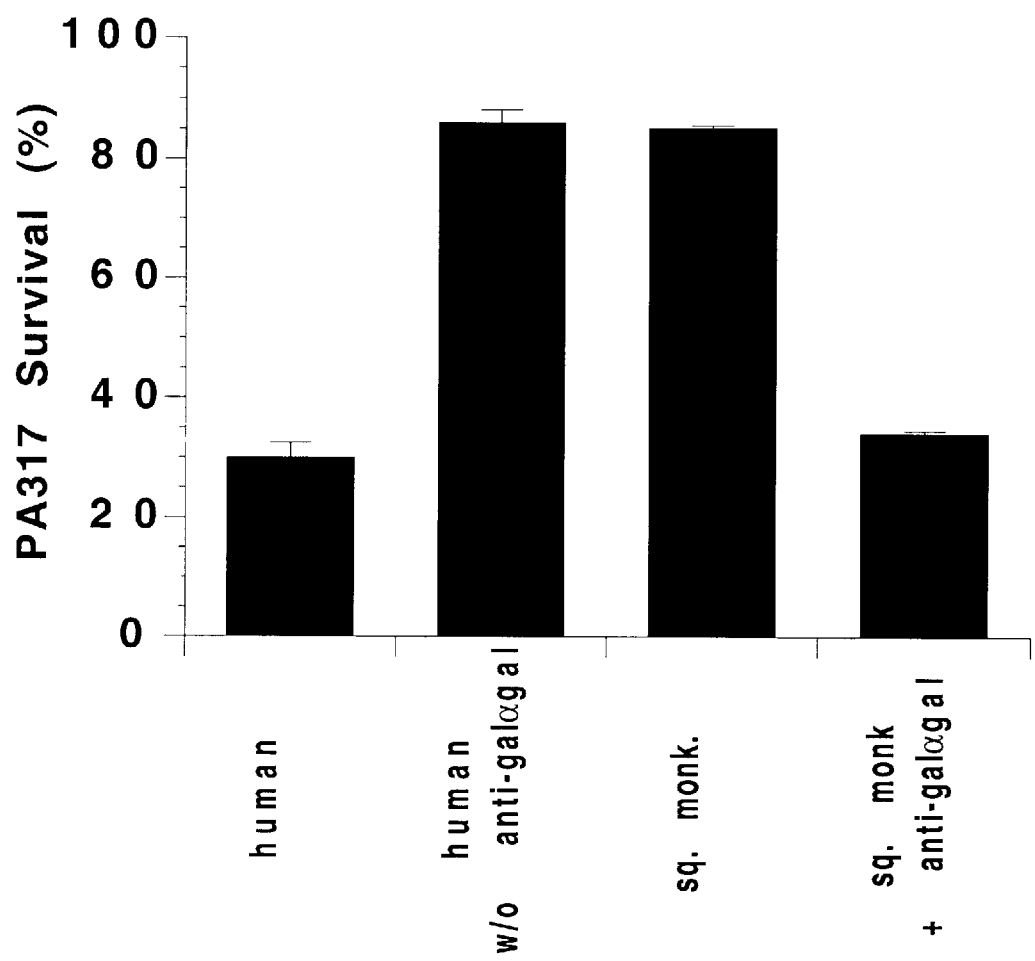
Figure 5B:
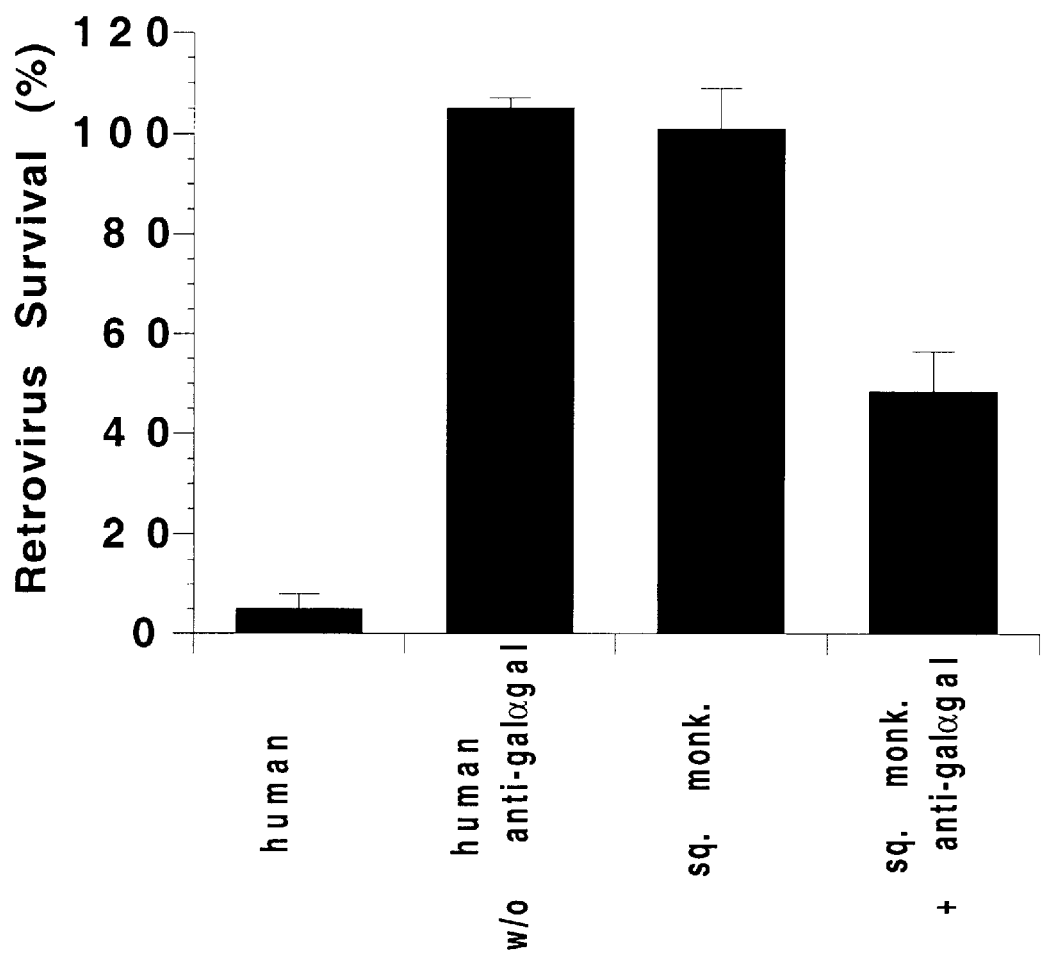

FIG. 5 shows the role of anti-αgalactosyl antibody in complement-mediated killing of PA317 producer cells and retrovirus. In Panel A, Calcein AM dye loaded PA317 producer cells were incubated with 20% human serum (human), 20% anti-αgalactosyl antibody depleted human serum (w/o anti-GalαGal), 20% squirrel monkey serum (sq. monk.) or 20% squirrel monkey serum containing purified human anti-αgalactosyl antibody (+anti-galαgal) and dye release was measured. Bars represent percent survival of PA317 cells calculated as the percent dye retained relative to total cell associated dye. In Panel B, the LXSN amphotropic retroviral particles generated from the PA317 producer cells were incubated with the same sera listed above at a concentration of 40%. Retrovirus survival was then determined in the retrovirus killing assay (see Materials and Methods). Bars represent the percentage of infectious particles remaining relative to input virus. Data represent duplicate determinations from a single experiment, one of two so performed. Error bars denote standard error or the mean.

Figure 6:
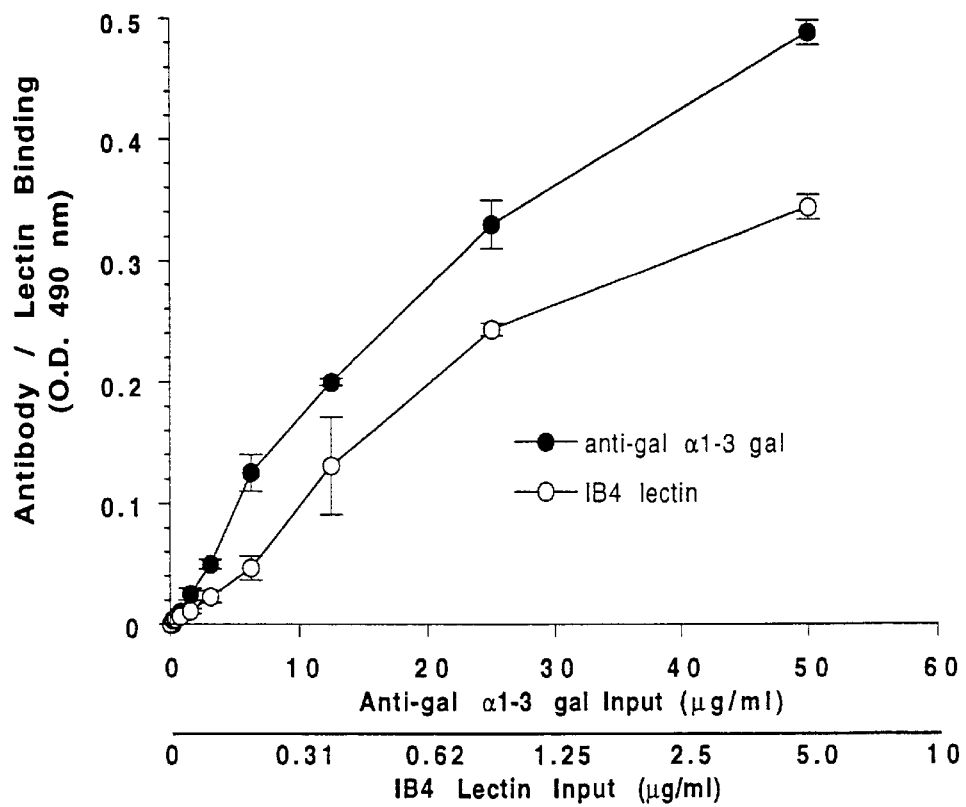

FIG. 6 shows analysis of αgalactosyl epitope expression on retrovirus by ELISA. Amphotropic supernatants were added to plates coated with Fab directed against the amphotropic gp70 envelope protein and subsequently reacted with either anti-αgalactosyl antibody or biotinylated $IB_4$ lectin (amounts indicated on the abscissa). Binding of antibody and lectin (indicated on the ordinate) was determined after development in the appropriate horseradish peroxidase-conjugated secondary reagent. Absorbance values were corrected for background absorbance using identically treated wells in the absence of retroviral particles. Data represent duplicate determinations from a single experiment, one of two so performed. Error bars denote standard error of the mean.

Figure 7A:
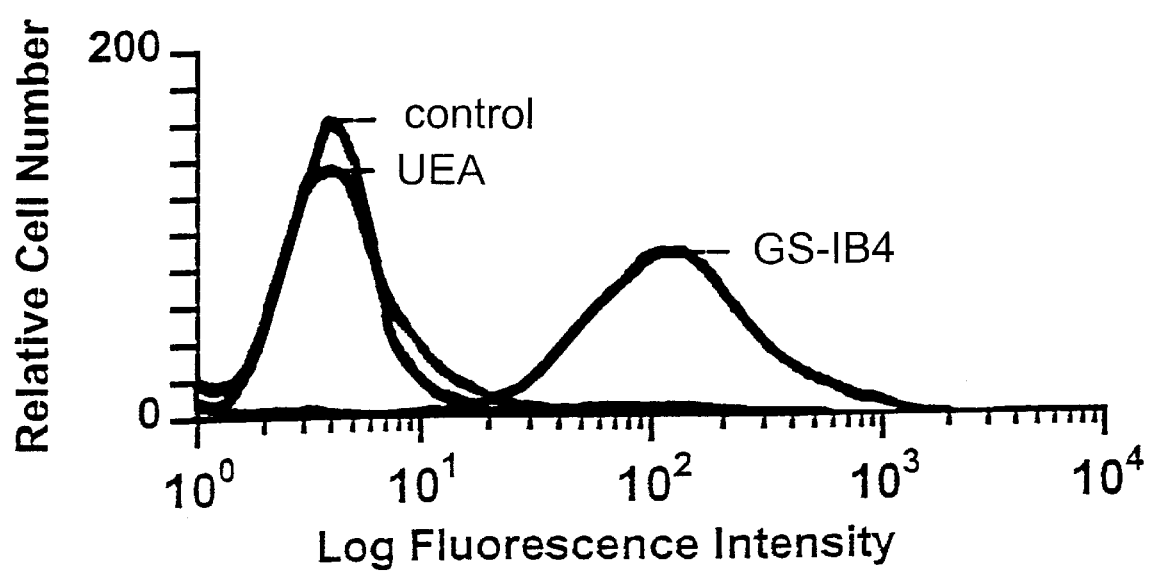
Figure 7B:
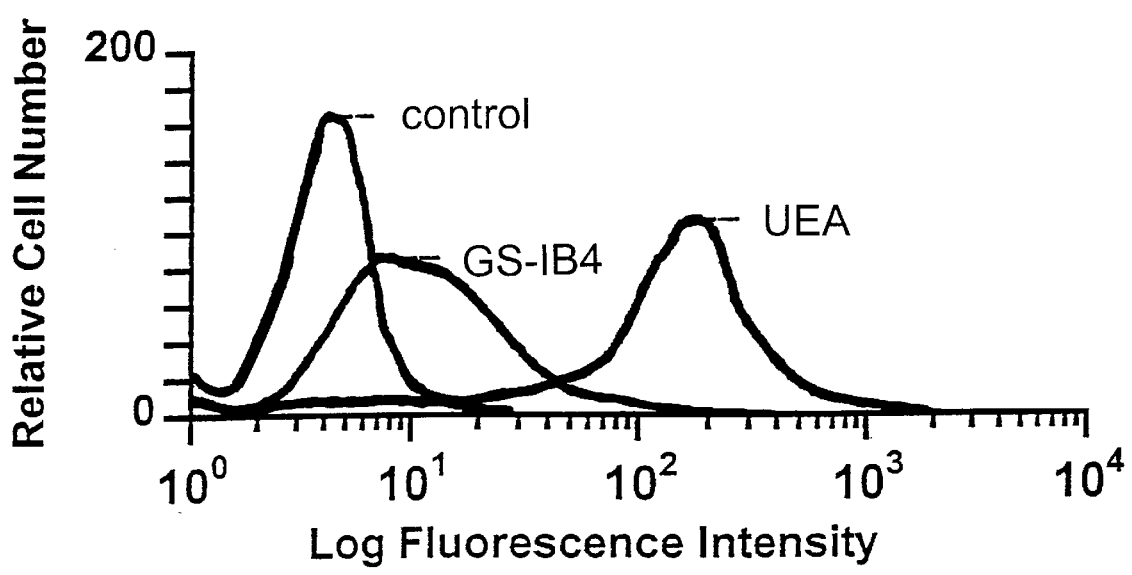
Figure 7C:
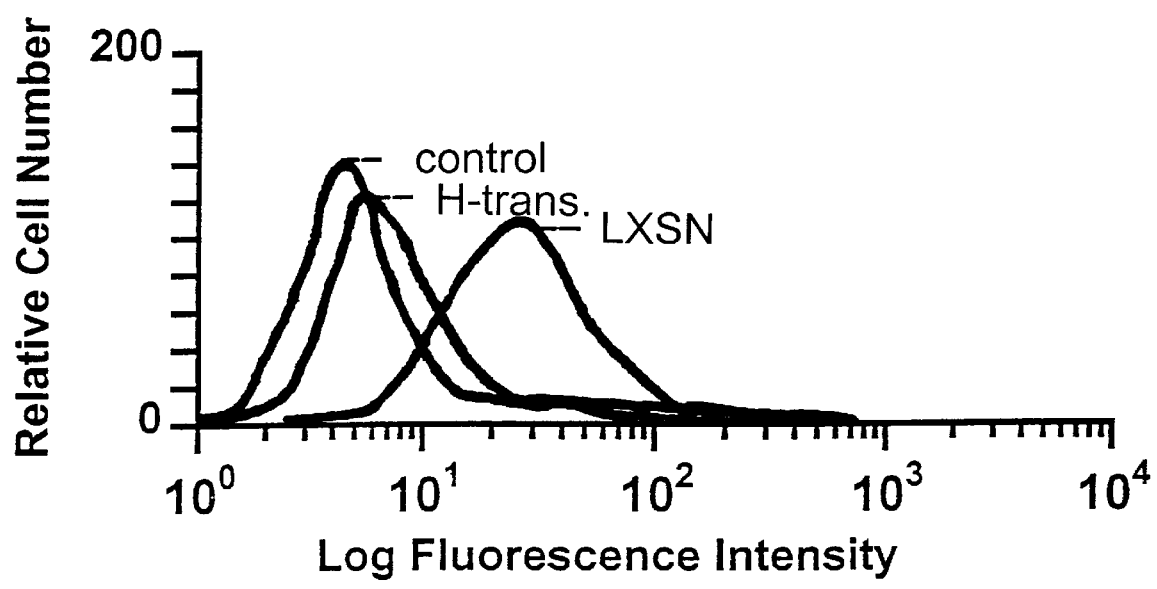

FIG. 7 shows FACS analysis of αgalactosyl epitope expression in PA317/H-transferase transductants. The PA317 amphotropic packaging cell line was transduced with either H-transferase or the pLXSN vector alone and selected with G418. Transduced cells were reacted with $GS-IB_4$ lectin, UEA lectin or anti-αgalactosyl antibody and analyzed by FACS (see Materials and Methods). UEA lectin staining (UEA) indicates expression levels of the H-transferase product (H-antigen) while $GS-IB_4$ lectin staining ($GS-IB_4$) indicates αgalactosyl epitope expression. Panel A and B show lectin binding to PA317 cells transduced with the LXSN vector alone or H-transferase, respectively. Unstained cells are indicated in each panel (control). Panel C shows the reactivity of PA317 cells transduced with H-transferase (H-trans.) or LXSN vector alone (LXSN) with the purified anti-αgalactosyl Ab. H-trans. cells incubated with secondary antibody alone are also shown (control).

Figure 8A:
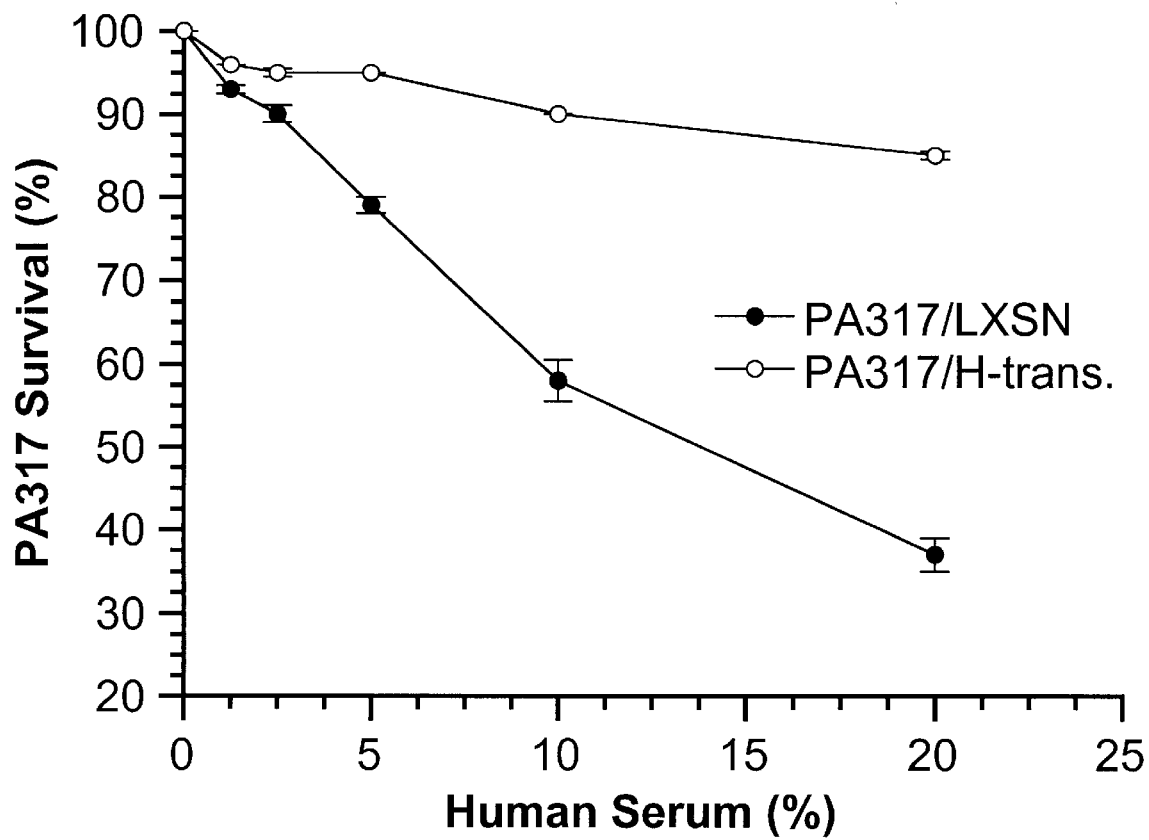
Figure 8B:
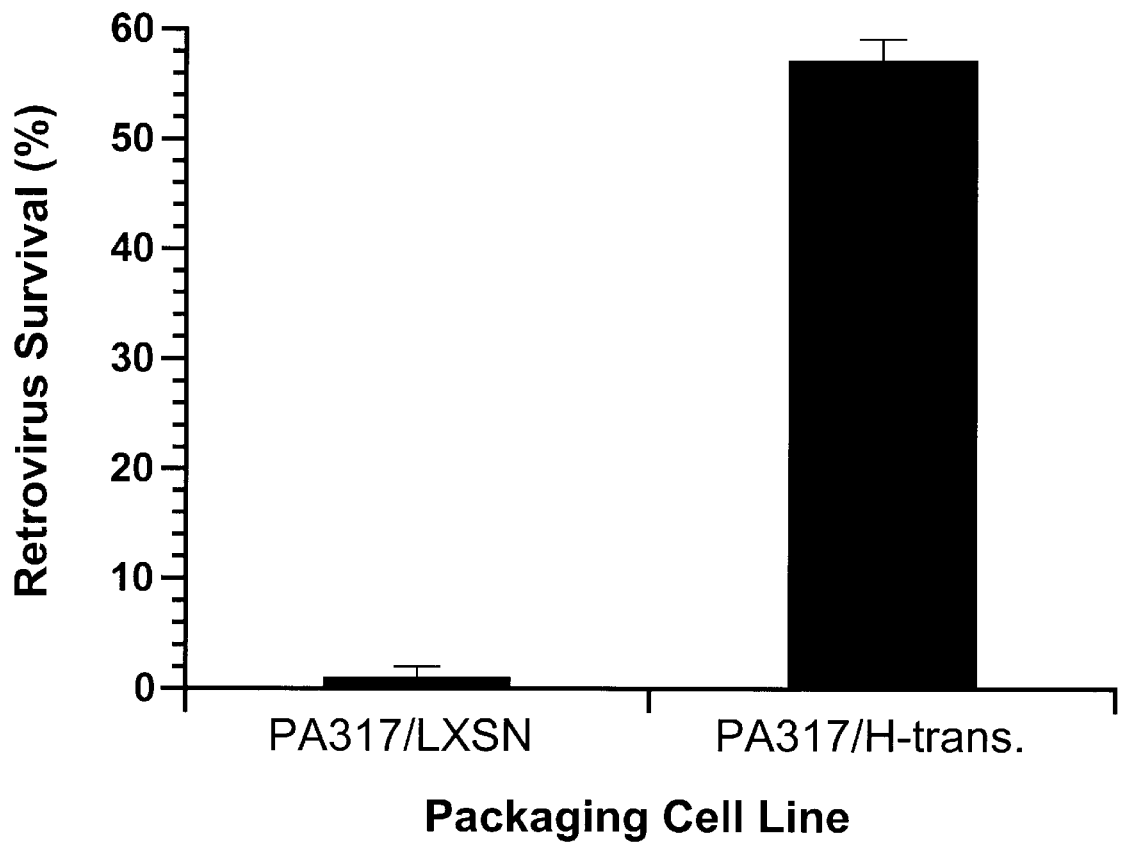
Figure 9A:
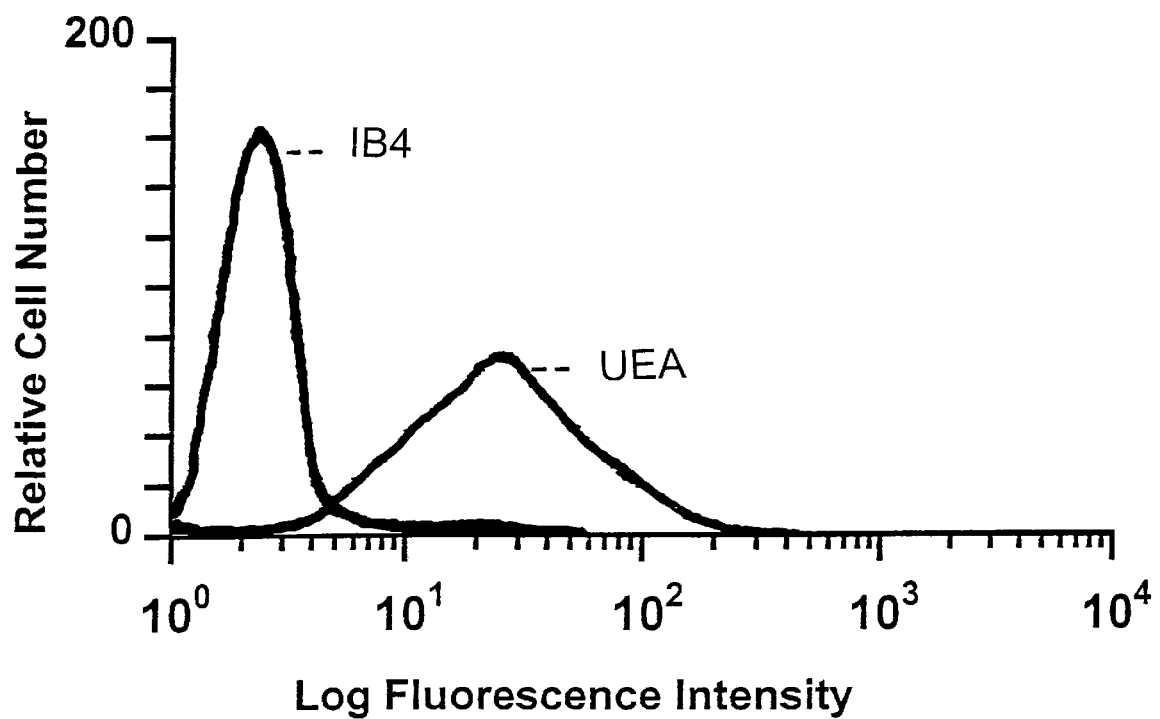
Figure 9B:
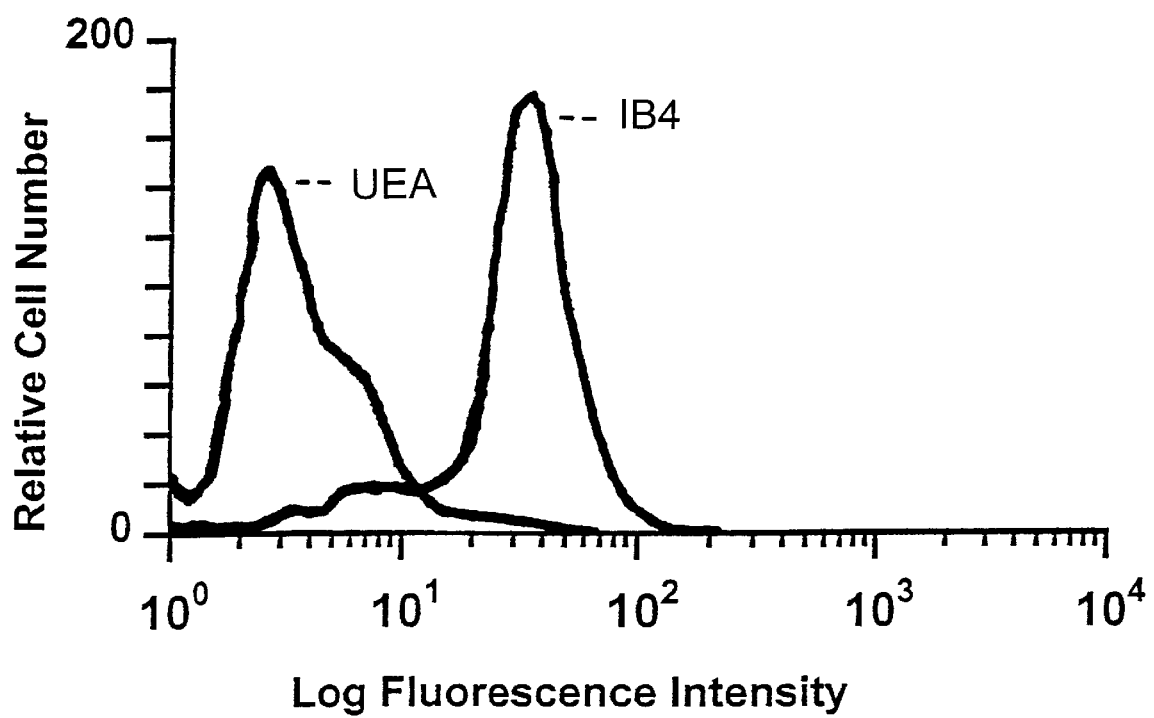
Figure 9C:
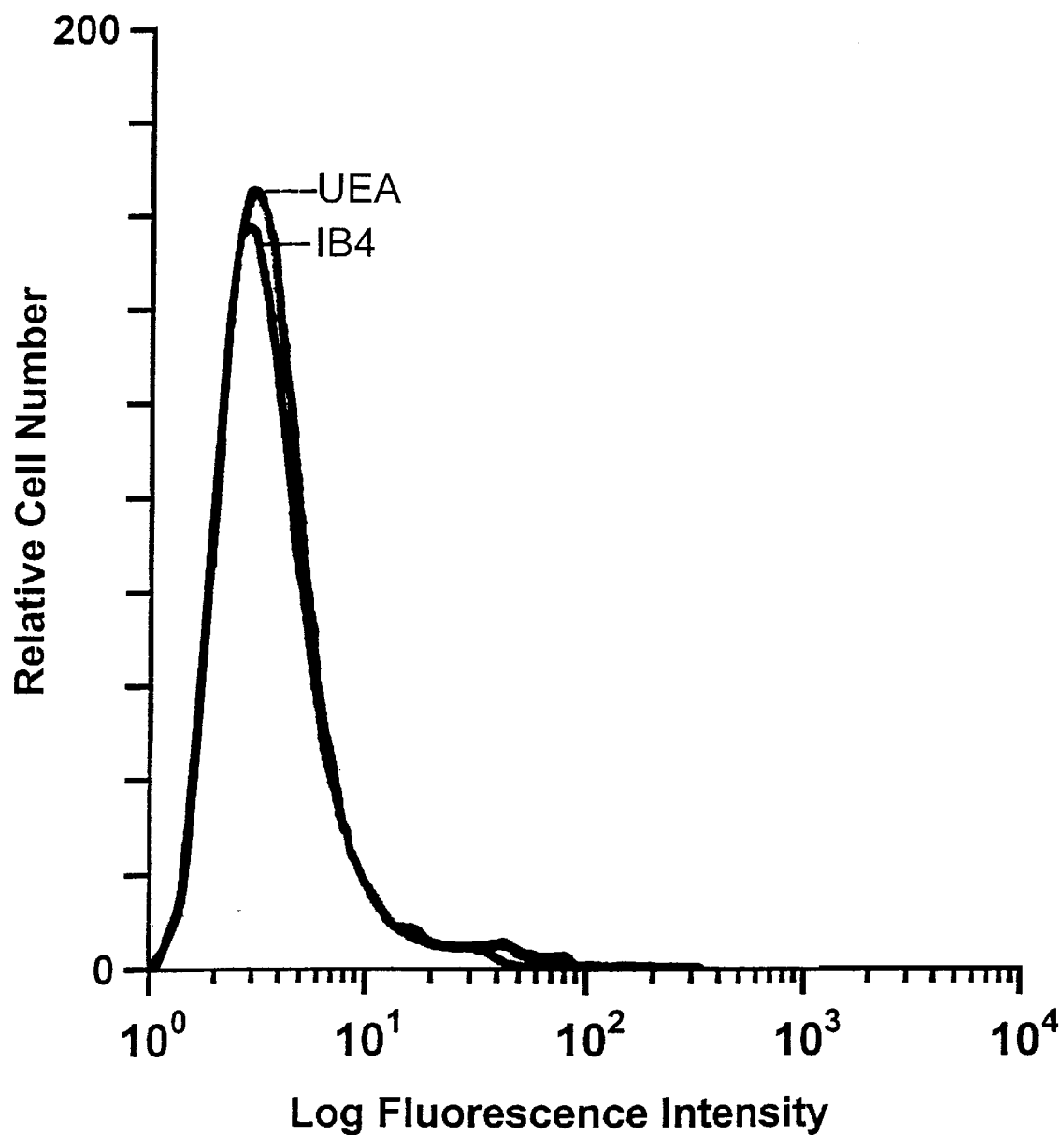
Figure 9D:
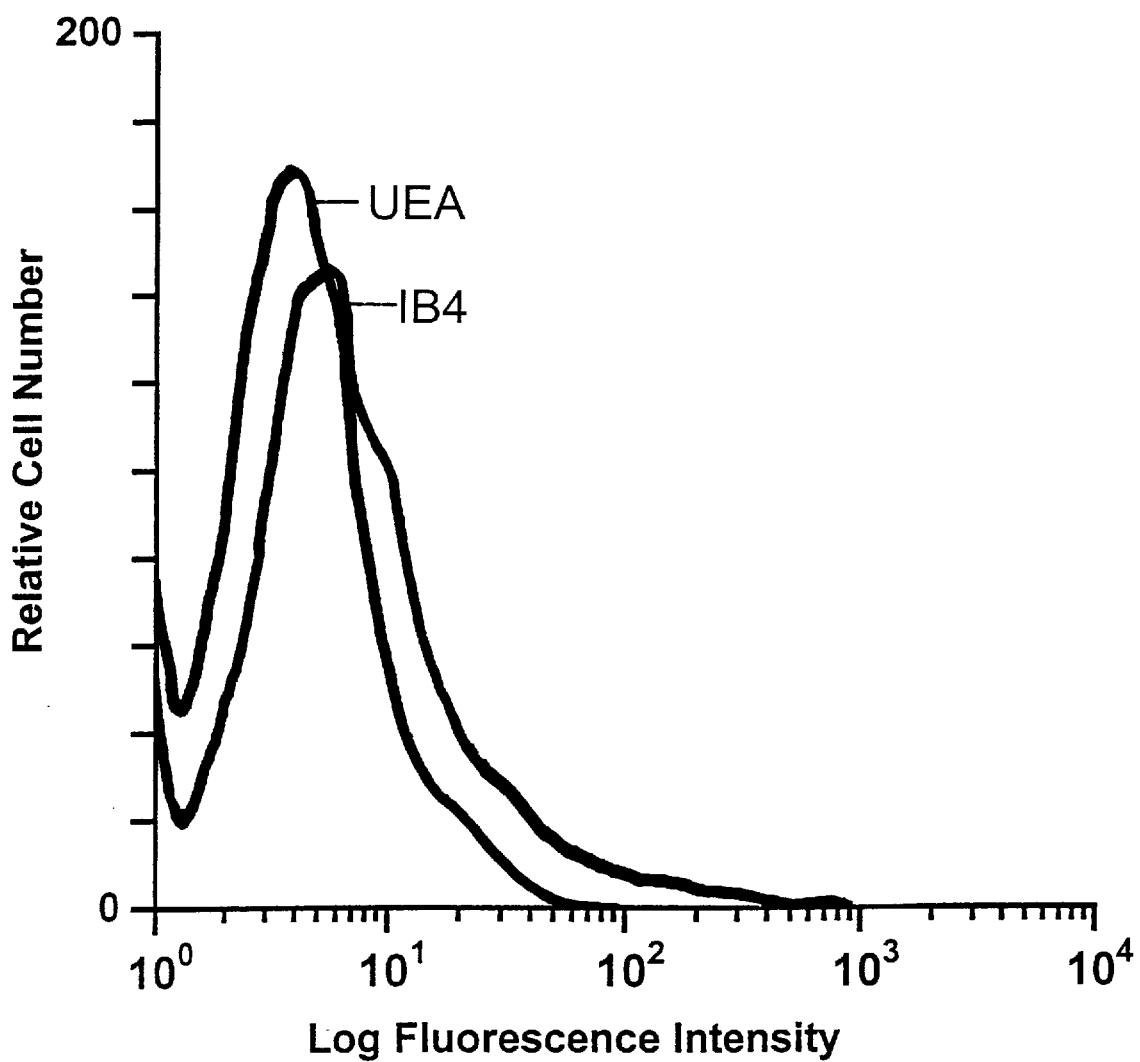

FIG. 8 shows serum sensitivity of PA317/H-transferase producer cells and retrovirus following αgalactosyl epitope downregulation. (A) PA317 cells transduced with either H-transferase (PA317/H-transferase) or the LXSN vector alone (PA317/LXSN) were subjected to a complement-mediated dye release assay. Curves represent PA317 cell survival at increasing concentrations of human serum calculated as the percent dye retained relative to total cell associated dye. (B) Retroviral particles liberated from PA317 cells transduced with H-transferase (PA317/H-trans.) or the LXSN vector alone (PA317/LXSN) were subjected to 40% human serum in a retrovirus killing assay. Bars represent the percentage of infectious vector particles remaining relative to input virus. Data represent duplicate determinations of a single experiment, one of two so performed. Error bars denote standard error of the mean.

FIG. 9 shows flow cytometry analysis. IB4 (GS-IB4) or UEA fluorescence staining of human HELA cells (FIG. 9a), CHO LEC8 cells (FIG. 9b), CHO-DG44 cells (FIG. 9c), and BHK-21 cells (FIG. 9d) for the cell surface expression of galactose alpha (1,3) galactosyl epitopes. These epitopes are identified by staining these cells with FITC conjugated IB4 lectin. FITC-conjugated UEA lectin is used to identify cell surface expression of the human H-eptitope (alpha-(1,2) fucosyl residues).

Figure 10:
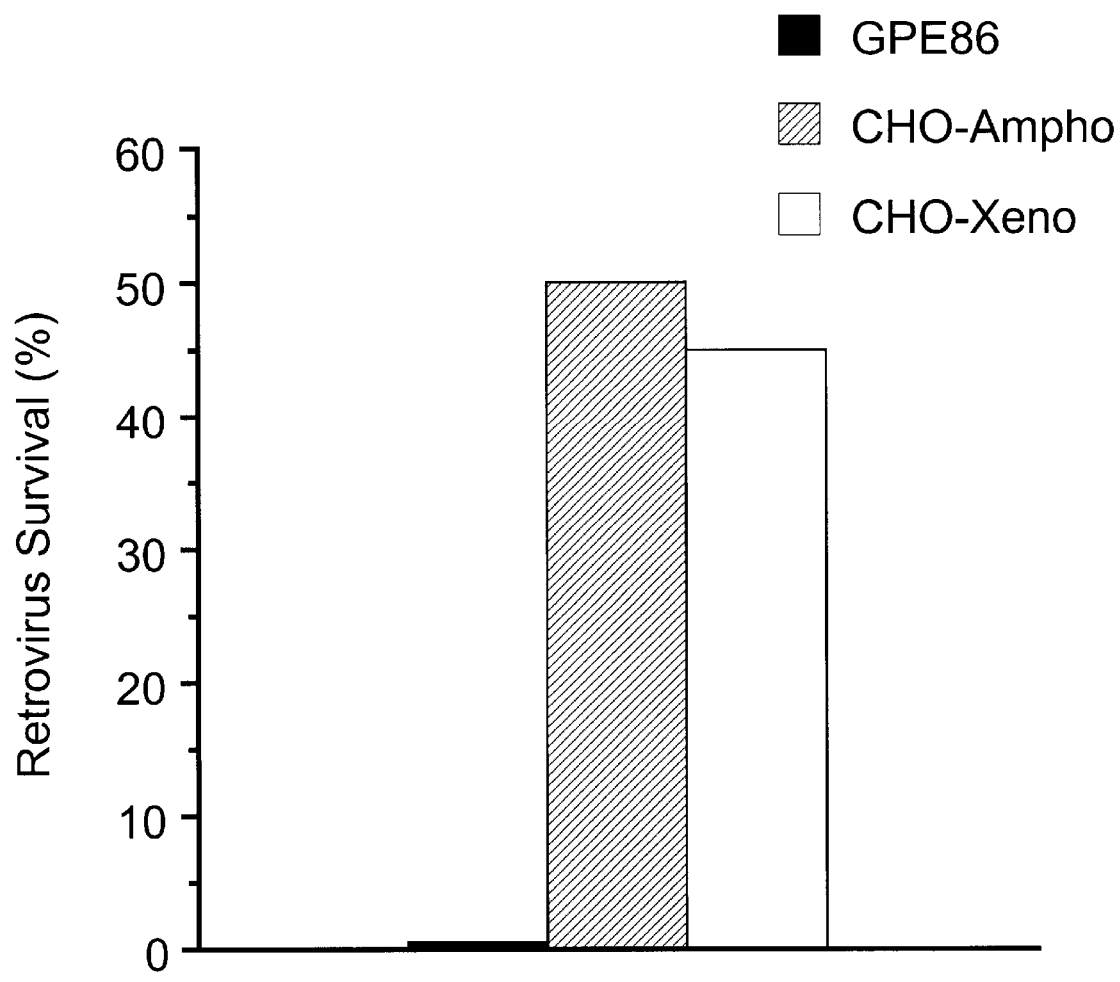

FIG. 10 shows retroviral vector particle survival in human serum. Retroviral particles were packaged and produced in murine GPE86 cells or in CHO-DG44 cells with either an amphotrophic or xenotrophic envelope. The RVVPs produced from the various producer cell lines were incubated with 50% human serum and then titered on appropriate indicator cells to assess survival. Bars indicate the percentage of transducing RVVPs surviving relative to RVVPs treated with heat-inactivated human serum. Data represent a single experiment, one of two so performed.

Figure 11:
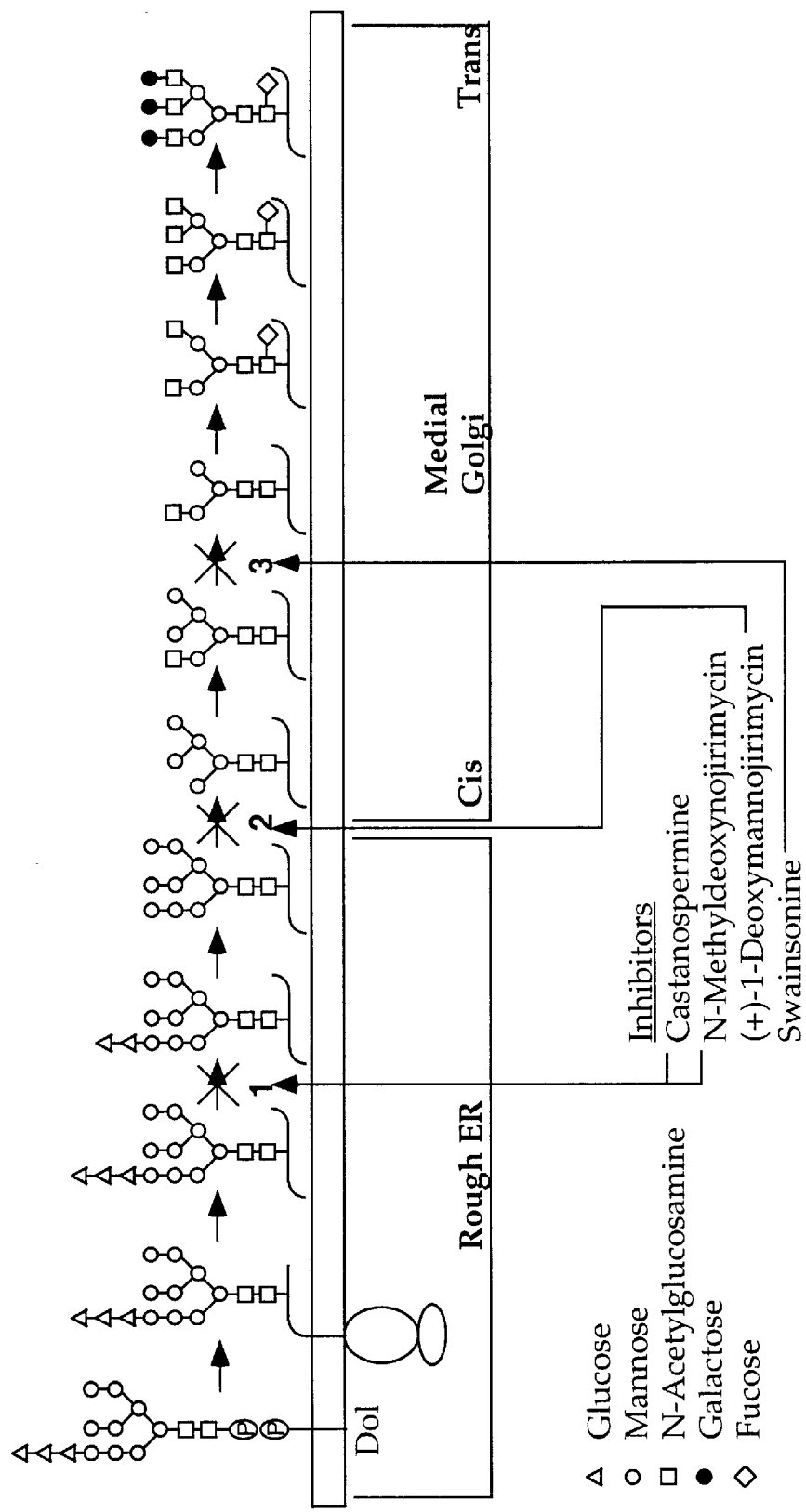

FIG. 11 shows a schematic representation of typical pathways for the formation of N-linked oligosaccharides. The precusor dolichol pyrophosphoryl oligosaccharide, $Glc_3,Man_9(GlcNAc)_2$ PP-Dol, is transferred to the nascent polypeptide at tripeptide motifs Asn-X-Ser or Asn-X-Thr by an oligosaccharide transferase enzyme. The precursor oligosaccharide is trimmed by one or both of two glucosidases (α-glucosidase I and α-glucosidase II) in the rough endoplasmic reticulum (RER) to yield $Man_9(GlcNAc)_2$. The resulting $Man_9(GlcNAc)_2$ is further trimmed by three mannosidases (RER α1-2 mannosidase I, Golgi α-mannosidase I, and Golgi α-mannosidase II). The activity of α-glucosidase I (1) has been shown to be greatly reduced by the addition of both castanospermine and N-methyldeoxynojirimycin. The activity of the Golgi α-mannosidase I (2) has been shown to be greatly reduced by the addition of 1-deoxymannojirimycin, while the activity of Golgi α-mannosidase II (3) has been shown to be greatly reduced by the addition of swainsonine. Finally, the complex type side chains are modified through the action of several different transferases in the medial and trans golgi. The final complex type shown in this figure is only one of many possible oligosaccharide side chains that can result from this pathway, however, this particular one is the substrate for an alpha (1,3) galactosyltransferase enzyme.

Figure 12:
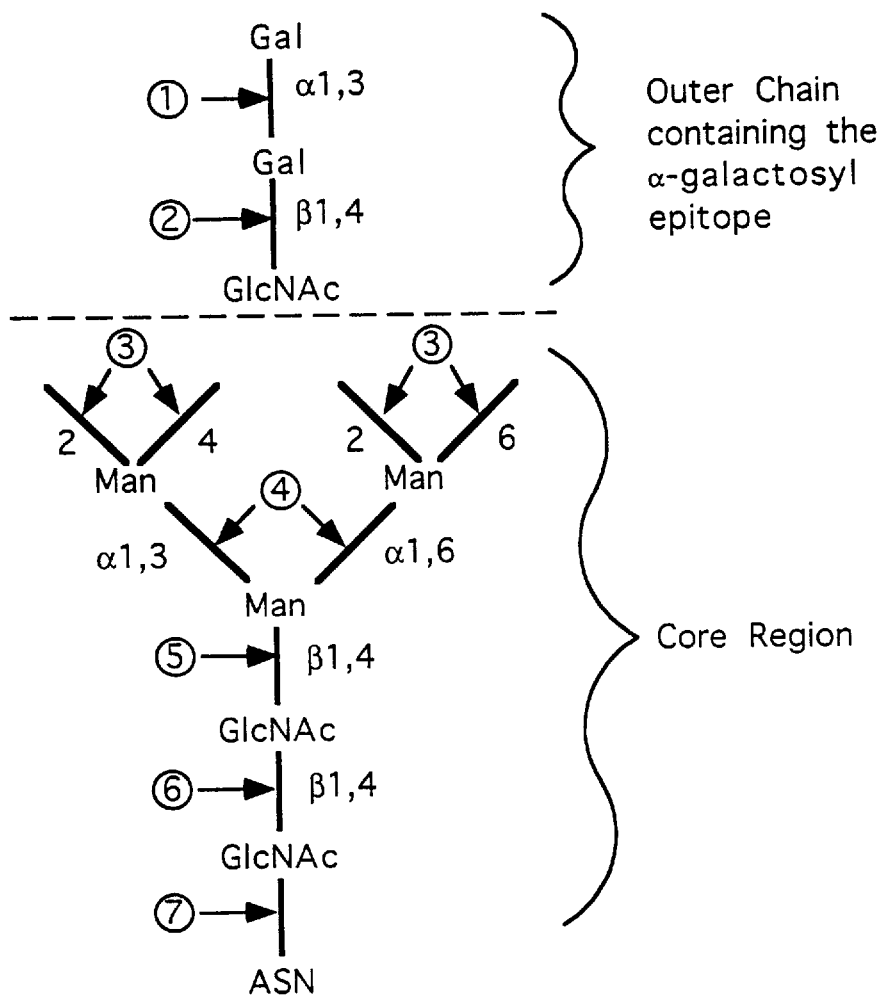

FIG. 12 shows the points of cleavage within carbohydrate molecules of various glycosidases and mannosidases. The outer chain shown contains the galactose alpha (1,3) galactosyl epitope, however, it is only one of many possible oligosaccharide modifications. The carbohydrate molecules that make up the side chain are abbreviated as follows: Gal, Galactose; GlcNAc, N-acetylglucosamine; and Man, Mannose. The type of bond between the carbohydrate molecules is indicated to the side of the bond and is specific for the alpha-galactosyl outer chain modification. The carbohydrate bond potentially susceptible to endo- or exoglycosidase or mannosidase treatment is shown as an arrow with the specific enzymes indicated by circled numbers as follows: 1) alpha-galactosidase (green coffee bean), 2) beta-galactosidase (Jack bean, *Streptococcus pneumoniae*, Bovine testes, or Chicken liver). 3) beta-N-Acetylhexosaminidase (*Streptococcus pneumoniae*, or Chicken liver), 4) a-mannosidase (Jack bean), 5) b-mannosidase (*Helix pomatia*), 6) Endoglycosidase H (*Streptomyces plicatus*), or Endoglycosidase F (*Flavobacterium meningosepticum*), and 7) Peptide-N-Glycosidase F (*Flavobacterium meningosepticum*).

The foregoing drawings, which are incorporated in and constitute part of the specification, illustrate certain embodiments of the invention, and together with the description, serve to explain the principles of the invention. It is to be understood, of course, that both the drawings and the description are explanatory only and Lare not restrictive of the invention.

DETAILED DESCRIPTION OF THE INVENTION

The present invention relates to gene therapy using retroviral vector particles. For ease of reference, the following abbreviations will be used in the discussion that follows: "IM" (inhibitor molecule) refers to a molecule that blocks the interaction of a galactose alpha (1,3) galactosyl epitope with an antibody binding to such an epitope; "ctPC" (chemically treated producer cell) refers to a producer cell that has been chemically treated by culturing in the presence of chemical inhibitor of carbohydrate synthesis; "crPC" (complement resistant producer cell) refers to a non-old-world-primate producer cell that exhibits reduced levels of carbohydrate structures comprising galactose alpha (1,3) galactosyl epitopes as compared to NIH 3T3 cells (ATCC designation CCL 163), the cell line from which most producer cells and packaging cells are typically derived; "protected PC" refers to a producer cell that has been protected from antibody binding, either because it is a ctPC or a crPC, or because it is bathed in fluids containing IMs; "crRVVP" (complement resistant RVVP) refers to an RVVP that has been obtained from a crPC or from a ctPC; "protected RVVP" refers to an RVVP that is either a crRVVP or is bathed in fluids containing IMs.

I. RVVPs:

General discussions of packaging cells, producer cells, retroviral vector particles and gene transfer using such particles can be found in various publications including PCT Patent Publication No. WO 92/07943, EPO Patent Publication No. 178,220, U.S. Pat. No. 4,405,712, Gilboa, 1986; Mann, et al., 1983; Cone and Mulligan, 1984; Eglitis, et al., 1988; Miller, et al., 1989; Morgenstern and Land, 1990; Eglitis, 1991; Miller, 1992; Mulligan, 1993, and Ausubel, et al., 1992. The manipulation of retroviral nucleic acids to construct packaging vectors and packaging cells is discussed in, for example, Ausubel, et al., Volume 1, Section III (units 9.10.1–9.14.3), 1992; Sambrook, et al., 1989; Miller, et al., 1989; Eglitis, et al., 1988; U.S. Pat. Nos. 4,650,764, 4,861, 719, 4,980,289, 5,122,767, and 5,124,263; as well as PCT Patent Publications Nos. WO 85/05629, WO 89/07150, WO 90/02797, WO 90/02806, WO 90/13641, WO 92/05266, WO 92/07943, WO 92/14829, and WO 93/14188. To form packaging cells, packaging vectors are introduced into suitable host cells such as those found in, for example, Miller and Buttimore, Mol. Cell Biol., 6:2895–2902, 1986; Markowitz, et al., J. Virol., 62:1120–1124, 1988; Cosset, et al., J. Virol., 64:1070–1078, 1990; U.S. Pat. Nos. 4,650,764, 4,861,719, 4,980,289, 5,122,767, and 5,124,263, and PCT Patent Publications Nos. WO 85/05629, WO 89/07150, WO 90/02797, WO 90/02806, WO 90/13641, WO 92/05266, WO 92/07943, WO 92/14829, and WO 93/14188. Once a packaging cell line has been established, producer cells are generated by introducing retroviral vectors into the packaging cells. Examples of such retroviral vectors are found in, for example, Korman, et al., 1987, Proc. Natl. Acad. Sci. USA, 84:2150–2154; Miller and Rosman, Biotechniques, 7:980–990, 1989; Morgenstern and Land, 1990; U.S. Pat. Nos. 4,405,712, 4,980,289, and 5,112,767; and PCT Patent Publications Nos. WO 85/05629, WO 90/02797, and WO 92/07943. The retroviral vector includes a psi site and one or more exogenous nucleic acid sequences selected to perform a desired function, e.g., an experimental, diagnostic, or therapeutic function. These exogenous nucleic acid sequences are flanked by LTR sequences which function as promoters and to direct high efficiency integration of the sequences into the genome of the ultimate target cell.

Many applications of gene therapy using retroviral vector particles (RVVPs) are known and have been extensively reviewed (see, for example, Boggs, 1990; Kohn, et al., 1989; Lehn, 1990, Verma, 1990; Weatherall, 1991; and Felgner and Rhodes, 1991).

A variety of genes and DNA fragments can be incorporated into RVVPs for use in gene therapy. These DNA fragments and genes may encode RNA and/or protein molecules which render them useful as therapeutic agents. Protein encoding genes of use in gene therapy include those encoding various hormones, growth factors, enzymes, lymphokines, cytokines, receptors, anti-tumor agents, and the like.

Among the genes which can be transferred are those encoding polypeptides that are absent, are produced in diminished quantities, or are produced in mutant form in individuals suffering from a genetic disease. Other genes of interest are those that encode proteins that, when expressed by a cell, can adapt the cell to grow under conditions where the unmodified cell would be unable to survive, or would become infected by a pathogen. Genes encoding proteins that have been engineered to circumvent a metabolic defect are also suitable for transfer into the cells of a patient. Such genes include the genes encoding the transmembrane forms of CD59 discussed in copending U.S. patent application Ser. No. 08/205,720, filed Mar. 3, 1994, entitled "Terminal Complement Inhibitor Fusion Genes and Proteins" and copending U.S. patent application Ser. No. 08/206,189, filed Mar. 3, 1994, entitled "Method for the Treatment of Paroxysmal Nocturnal Hemoglobinuria".

In addition to protein-encoding genes, RVVPs can be used to introduce nucleic acid sequences encoding medically useful RNA molecules into cells. Examples of such RNA molecules include anti-sense molecules and catalytic molecules, such as ribozymes.

In order to expedite rapid transduction by eliminating the need to wait for target cells to divide, and to allow transduction of cells that divide slowly or not at all, the use of RVVPs that can transduce non-dividing cells may be preferred. Such RVVPs are disclosed in copending U.S. patent applications Ser. Nos. 08/181,335 and 08/182,612, both entitled "Retroviral Vector Particles for Transducing Non- Proliferating Cells" and both filed Jan. 14, 1994. These patent applications also discuss specific procedures suitable for producing packaging vectors and retroviral vectors as well as the use of such vectors to produce packaging cells and producer cells, respectively.

II. Obtaining Protection of Retroviral Vector Particles and Producer Cells from Inactivation by the Humoral Immune System:

In order to be effective, retroviral vector particles (RVVPs), and, in some instances retroviral producer cells (PCs), need to be protected from(inactivation or destruction) by the action of complement in the body fluids of a host organism. The preset invention provides a variety of methods and compositions that allow such protection of RVVPs and PCs to be achieved.

Screening In accordance with the invention in certain of its aspects, such protection is achieved by preparing crRV-VPs using producer cells which have been selected based on screening assays that are used to detect producer cells that are deficient in galactose alpha (1,3) galactosyl epitopes compared to NIH 3T3 cells (ATCC designation CCL 163). The RVVPs that bud from such galactose alpha (1,3) galactosyl-deficient producer cells will themselves be deficient for this carbohydrate epitope and will, therefore, be crRVVPs, and protected from antibody and complement-mediated virolysis.

In accordance with this embodiment of the present invention, protected packaging cells, protected PCs, and protected RVVPs derived therefrom are obtained using non-primate cell lines lacking expression of the galactose alpha (1,3) galactosyl epitope. Preferred cell lines for such selection include certain Chinese hamster ovary (CHO) and baby hamster kidney (BHK) cell lines that have been reported to exhibit metabolic alterations in glycosylation (Goochee et. al., 1991). As shown in FIG. 9, CHO LEC8 cells express alpha galactosyl epitopes (and consequently are not preferred for this embodiment of the invention), while CHO DG44 cells do not express detectable alpha galactosyl epitopes (and consequently are preferred for this embodiment of the invention). As also shown in FIG. 9, human HeLa cells do not express detectable alpha galactosyl epitopes (but are not preferred for this embodiment of the invention, as human cells and products derived therefrom pose safety problems in therapeutic settings), and BHK-21 cells do not express detectable alpha galactosyl epitopes (and consequently are also preferred for this embodiment of the invention). Other cells exhibiting such metabolic deficiencies can be obtained by screening in accordance with the invention. Significantly, non-human, non-Old World primate cells exhibiting such metabolic deficiencies have not previously been used as starting materials for the derivation of packaging cells, producer cells, or RVVPs.

Glycosylation Inhibitor Treatment crRVVPs can be prepared using producer cells that have been treated with inhibitors of intracellular glycosylation so as to prevent the synthesis of the galactose alpha (1,3) galactosyl epitope by the cells. Preferred inhibitors are compounds that act by blocking the actions of the various glucosidases and mannosidases involved in the processing of high mannose side chains to produce complex or hybrid side chains.

Such inhibitors are well known in the art and can be used in order to block the progression of the metabolic pathway at the various stages of oligosaccharide modification. These agents generally fall into three chemical groups: indolizidine alkaloids (swainsonine [SWS] and castanospermine [CS]), polyhydroxylated pyrrolidines and piperidenes (N-Methyldeoxynojirimycin [MdN] and 1-deoxymannojirimycin [DMM]), and myoinositol derivatives. These compounds, which are typically isolated form the seeds of leguminous plants, are commercially available from sources such as Oxford Glycosystems (Rosedale, N.Y.).

Preferred inhibitors will meet the following two criteria: 1) the inhibitor should not be cytotoxic at a glycosylation inhibitory concentration; 2) the inhibitor should not completely eliminate all glycosylation, but should inhibit the expression of the galactose alpha (1,3) galactosyl epitope by the cells. Preferably the inhibitor will block the glycosylation pathway prior to the addition of N-acetylglucosamine in order to down regulate the availability of substrate for the alpha (1,3) galactosyltransferase enzyme.

Examples of such inhibitors of glycosylation include deoxymannojirimycin, swainsonine, castanospermine, deoxynojirimycin, N-methyldeoxynojirimycin, 2,5-dihydroxymethyl-3,4-dihydroxypyrrolidine,1,4-dideoxy-1,4-imino-D-mannitol hydrochloride, australine, and bromo-conduritol. These glycosylation inhibitors can be obtained commercially from numerous sources including Oxford Glycosystems (Rosedale, N.Y.), and are typically used by adding them, preferably according to the manufacturer's directions, to the fluids bathing the cells in which specific inhibition of glycosylation is desired.

Other glycosylation inhibtors that act to block earlier steps in the glycosylation pathway, and therefore provide a more extensive blockade of glycosylation, are also known in the art, e.g., tunicamycin. These inhibitors include compounds that can completely block glycosylation, and are not preferred for use in the various aspects of the present invention. For discussion of the deleterious effects of tunicamycin on viruses see Pizer, et al. 19890 and Delwart et al. 1990.

Treatment With Glycolytic Enzymes Galactose alpha (1,3) galactosyl epitopes can be enzymatically removed by specific endo- or exo-glycosidases and mannosidases. Such glycolytic enzymes and general methods for their use are well known in the art (Kornfeld and Kornfeld, 1985). crRVVPs can be obtained from RVVPs produced in non-Old World primate cells and subsequently or concurrently treated with specific glycosidases and mannosidases to remove galactose alpha (1,3) galactosyl epitopes from the RVVPs. Examples of glycosidases and mannosidases suitable for use in this aspect of the invention include alpha- or beta-galactosidase, beta-N-acetylhexosaminidase, alpha- or beta-mannosidase, endoglycosidase H or F, and peptide-N-glycosidase F. These enzymes are all commercially available from Oxford Glycosystems (Rosedale, N.Y.), and are typically used according to the manufacturer's instructions.

Recombinant Modification crRVVPs can be prepared using producer cells which have been genetically modified to contain exogenous nucleic acid molecules designed to reduce the expression of galactose alpha (1,3) galactosyl epitopes by the producer cells. The preparation of certain of such producer cells is discussed in copending U.S. patent application Ser. No. 08/278,282, entitled "Methods for Reducing Hyperacute Rejection of Xenografts", filed Jul. 21, 1994 in the names of Mauro S. Sandrin, William L. Fodor, Russell P. Rother, Stephen P. Squinto, and Ian F. C. McKenzie, the relevant portions of which are incorporated herein by reference. As discussed therein, the nucleic acid molecules used to prepare these producer cells include plasmids encoding polypeptides providing H-transferase activities.

Alternatively, exogenous nucleic acid molecules designed to specifically inhibit the expression of the native galactose alpha (1,3) galactosyl transferase enzyme within a cell from which the protected producer cells are derived may be used. These genetic manipulations include the use of nucleic acid molecules specially engineered to allow gene inactivation using antisense RNAs, antisense oligonucleotides, and gene knockout techniques.

Antisense RNAs can be used to specifically inhibit gene expression (see, for example, Eguchi, et al., 1991). Such RNA molecules can be expressed by recombinant nucleic acid molecules engineered for expression in packaging or producer cells.

Antisense nucleic acid molecules in the form of oligo-nucleotides (including oligonucleotide analogs) and derivatives thereof can also be used to specifically inhibit gene expression, as described, for example, in Cohen, 1989. As described therein, antisense oligonucleotides can be designed and used to inhibit expression of specific genes (Cohen, 1989, pp. 1–6, 53–77).

Such antisense oligonucleotides can be in the form of oligonucleotide analogs, for example, phosphorothioate analogs (Cohen, 1989, pp. 97–117), non-ionic analogs (Cohen, 1989, pp. 79–95), and a-oligodeoxynucleotide analogs (Cohen, 1989, pp. 119–136). Derivatives of oligonucleotides that can be used to inhibit gene expression include oligonucleotides covalently linked to intercalating agents or to nucleic acid-cleaving agents (Cohen, 1989, pp. 137–172), and oligonucleotides linked to reactive groups (Cohen, 1989, pp. 173–196). Oligonucleotides and derivatives designed to recognize double-helical DNA by triple-helix formation (Cohen, 1989, pp. 197–210) may also be used to specifically inhibit gene expression.

All of the oligonucleotides and derivatives described above are used by adding them to the fluids bathing the cells in which specific inhibition of gene expression is desired.

Another method to reduce the expression of galactose alpha (1,3) galactosyl epitopes is to perform genetic manipulations referred to in the art as "gene disruption" or "gene knockout." Gene knockout is a method of genetic manipulation via homologous recombination that has long been carried out in microorganisms, but has only been practiced in mammalian cells within the past decade. These techniques allow for the use of specially designed DNA molecules (gene knockout constructions) to achieve targeted inactivation (knockout) of a particular gene upon introduction of the construction into a cell.

The practice of mammalian gene knockout, including the design of gene knockout constructions and the detection and selection of successfully altered mammalian cells, is discussed in numerous publications, including Thomas, et al., 1986; Thomas, et al., 1987; Jasin and Berg, 1988; Mansour, et al., 1988; Brinster, et al., 1989; Capecchi, 1989; Frohman and Martin, 1989; Hasty, et al., 1991; Jeannotte, et al., 1991; and Mortensen, et al., 1992.

Further discussions of gene knockouts can be found in copending U.S. patent application Ser. No. 08/214,580 entitled "Xenotransplantation Therapies" filed Mar. 15, 1994 and copending U.S. patent application Ser. No. 08/252,493 entitled "Porcine E-Selectin" filed Jun. 1, 1994, the relevant portions of which are incorporated herein by reference.

In general, to form packaging cells to be used in accordance with these recombinant modification aspects of the present invention, a nucleic acid molecule designed to effect a reduction of the expression of galactose alpha (1,3) galactosyl epitopes is introduced into cells from which the packaging cells of the invention are to be derived, either before or after the introduction of the packaging vector or vectors discussed above under the subheading "RVVPs". The producer cells of the invention are then prepared by the introduction of a retroviral vector into the packaging cells of the invention.

Alternatively, the genetic manipulations leading to the protection of RVVPs may be carried out directly in producer cells without the intermediate step of preparing packaging cells that have been so modified. The packaging cell approach is generally preferred. In either case, the producer cells themselves have enhanced resistance to complement which is of value when such cells are to be implanted in a patient (see below).

The genetically modified producer cells are generally used to produce RVVPs by culturing of the cells in a suitable growth medium. If desired, the particles can be harvested from the culture and administered to the target cells that are to be transduced, or the producer cells can be grown together with the target cells. The growth of producer cells together with target cells can be accomplished by co-culture of the cells in vitro, or, when desired, by implantation of the producer cells in the patient (see further discussion below).

Inhibitory Molecules In accordance with other aspects of the present invention, inhibitory molecules (IMs) can be used to protect RVVPs and/or producer cells. The IMs can be used alone or in combination with RVVPs and/or producer cells which are themselves at least partially protected from complement attack.

IMs are antagonists of antibody binding to antigens comprising galactose alpha (1,3) galactosyl epitopes. Various mechanisms may be associated with the actions of IMs. These include binding or association with the antibody reactive site and change of conformation of the antibody reactive site, such as by binding to residues associated with, adjacent to, or distanced from the active site, which effect the conformation of the active site such that it is incapable of binding the galactose alpha (1,3) galactosyl epitope or binds the epitope with reduced affinity. For example, in accordance with techniques well known in the art (see, for example, Coligan, et al., eds. Current Protocols In Immunology, John Wiley & Sons, New York, 1992; Harlow and Lane, Antibodies, A Laboratory Manual, Cold Spring Harbor Laboratory, New York, 1988; and Liddell and Cryer, A Practical Guide To Monoclonal Antibodies, John Wiley & Sons, Chichester, West Sussex, England, 1991), such a change of the conformation of the antibody reactive site can be achieved through the use of an anti-idiotypic antibody raised against an antibody binding to galactose alpha (1,3) galactosyl epitope or fragments of such an antibody. As is also well known in the art, these anti-idiotypic antibodies may be modified to enhance their clinical usefulness, for example by enzymatic techniques such as preparing Fab' fragments, or by recombinant techniques such as preparing chimeric, humanized, or single chain antibodies.

This invention is not limited to any specific IM, and any IM which is non-toxic and which modulates the interaction between antibodies and galactose alpha (1,3) galactosyl epitopes may be used in this invention. Preferred IMs are carbohydrates. Suitable examples of carbohydrate IMs include galactose alpha-1,3 galactose, D-galactose and melibiose, stachyose and methyl-a-D-galactopyranoside, D-galactosamine, and derivatives thereof. The term derivatives encompasses, for example, any alkyl, alkoxy, alkylkoxy, aralkyl amine, hydroxyl, nitro, heterocycle, sulphate and/or cycloalkyl substituents whether taken alone or in combination, which derivatives have IM activities.

IM activities provide a substantial reduction in RVVP inactivation by human or Old World primate body fluids as assessed according to the methods herein described. Carbohydrate polymers containing one or more of the aforesaid carbohydrate moieties or derivatives may also act as IMs and may be utilized in the practice of this invention. Further discussions of carbohydrate molecules that can be used as IMs may be found in U.S. patent application Ser. No. 08/214,580, entitled "Xenotransplantation Therapies", filed by Mauro S. Sandrin and Ian F. C. McKenzie on Mar. 15, 1994, and those discussed in PCT publication No. 93/03735, entitled "Methods and Compositions for Attenuating Antibody-Mediated Xenograft Rejection", both of which are incorporated herein by reference.

III. Preferred Levels of Protection The complement resistant RVVPs of the invention and/or the RVVPs treated with inhibitory molecules (i.e., the protected RVVPs) are substantially protected from inactivation in that they exhibit a substantial reduction of inactivation upon exposure to the body fluids of the patient, i.e., the body fluids of a human or Old World primate. An at least 5% reduction will, in general, comprise a "substantial reduction". Smaller reductions are also considered "substantial" if they represent a statistically significant reduction, i.e., a reduction that, when obtained in replicate assays and analyzed by a conventional statistical test, such as the student's T test, will give a probability value, p, which is less than or equal to 0.05, and, preferably, less than or equal to 0.015.

The substantial nature of such apparently small reductions is due to the huge numbers of RVVPs that can be prepared using conventional methods. RVVP titers of greater than $10^9$ RVVPs per ml can be prepared by concentration (e.g., by tangential flow filter concentration) of RVVP containing supernatants obtained using retroviral transduction systems known in the art.

As an example, a 100% inactivation may be obtained in the presence of a body fluid, and a 1% reduction in RVVP inactivation may be achieved using a protected RVVP, as compared to an unprotected RVVP. In such a case, if 1 ml of a $10^9$ RVVP per ml preparation is administered to the body fluid, no RVVPs will be present when unprotected RVVPs are administered, and ten million RVVPs will be present in the body fluid when the protected RVVPs of the invention are administered.

While RVVPs that are substantially protected are thus useful, RVVPs that exhibit an at least 50% reduction of inactivation upon exposure to human or Old World primate body fluids are particularly preferred.

IV. Use and Administration of Protected RVVPs The protected RVVPs of the invention can be used for gene therapy in accordance with various ex vivo techniques known in the art. In general terms, these techniques involve the removal of target cells of interest from a patient, incubation of the target cells with the retroviral vector particles, and reintroduction of the transduced target cells into the patient. Various procedures can be applied to the target cells while they are in the ex vivo state, including selection of subsets of the target cells prior to transduction, isolation of transduced cells, selection of subsets of isolated, transduced cells, propagation of target cells either before or after transduction, in cases where the cells are capable of proliferation, and the like. Delivery of nucleic acid molecules of interest may also be accomplished in vivo by administration of the protected retroviral vector particles to a patient.

In connection with such in vivo or ex vivo administration, retroviral vector particles can be pre-treated in accordance with the procedures discussed in co-pending application Ser. No. 08/098,944, filed Jul. 28, 1993, in the name of James M. Mason and entitled "Pre-binding of Retroviral Vector Particles with Complement Components to Enable The Performance of Human Gene Therapy In Vivo."

Similarly, the procedures of copending U.S. patent application Ser. No. 08/278,550, entitled "Retroviral Transduction of Cells Using Soluble Complement Inhibitors", filed Jul. 21, 1994 in the names of Russell P. Rother, Scott A. Rollins, James M. Mason, and Stephen P. Squinto and copending U.S. patent application Ser. No. 08/278,630, entitled "Retroviral Vector Particles Expressing Complement Inhibitor Activity", filed Jul. 21, 1994 in the names of James M. Mason and Stephen P. Squinto can be used in combination with the procedures of the present invention.

The administration to a patient of protected RVVPs, as well as the administration of the other pharmaceutical compositions of the invention, can be performed locally, e.g., by aerosol, transmucosal, or transdermal delivery, or, more typically, by a systemic route, e.g., orally, intravenously, intraperitoneally, intramuscularly, transdermally, intradermally, subdermally, transmucosally, or intrathecally. For systemic administration, injection is preferred.

The various RVVPs, cells, and compositions used in the practice of various aspects of the invention can be formulated as pharmaceutical compositions. Such compositions will generally include a pharmaceutically effective carrier, such as saline, buffered (e.g., phosphate buffered) saline, Hank's balanced salts solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like. See, for example, Remington's Pharmaceutical Sciences, Mack Publishing Company, Philadelphia, Pa., 17th ed., 1985.

The pharmaceutical compositions are suitable for use in a variety of drug delivery systems. Langer, Science, 249:1527–1533, 1990, reviews various drug delivery methods currently in use. In some cases, the drug delivery system will be designed to optimize the biodistribution and/or pharmacokinetics of the delivery of the retroviral vector particles. See, for example, Remington's Pharmaceutical Sciences, supra, Chapters 37–39. For example, the compositions can be incorporated in vesicles composed of substances such as proteins, lipids (for example, liposomes), carbohydrates, or synthetic polymers. See, for example, Langer, 1990, supra.

In certain preferred embodiments, the invention also provides articles of manufacture consisting of pharmaceutical compositions that contain the crRVVPs, crPCs, and/or IMs and packaging material indicating that the pharmaceutical composition is to be used in conjunction with the administration of RVVPs and/or gene therapy, as appropriate.

The pharmaceutical compositions of the invention can be administered in a variety of unit dosage forms. The dose will vary according to, e.g., the particular vector particle, producer cell and/or inhibitor molecule(s), the manner of administration, the particular disease being treated and its severity, the overall health and condition and age of the patient, and the judgment of the prescribing physician. Dosage levels for human subjects are generally between about $10^6$ and $10^{14}$ colony forming units of retroviral vector particles per patient per treatment. Producer cells are provided in amounts of at least $10^3$ to $10^4$ cells per treatment. IMs are provided in an amount sufficient to provide a concentration in the patient's body fluids (e.g., blood) that will substantially reduce the inactivation of RVVPs upon exposure to the body fluids of a patient in an in vitro assay such as those described below.

As discussed above, in certain cases gene therapy may be carried out by a procedure in which a retroviral producer cell (i.e., an engineered cell producing RVVPs) is implanted into the body of the patient to be treated. This may be a particularly desirable procedure in the treatment of certain cancers. For use in such cancer treatment procedures, a galactose alpha (1,3) galactosyl transferase gene may be used as a gene transduced into target tumor cells by RVVPs.

The cDNA coding for the galactose alpha (1,3) galactosyl transferase that transfers a terminal galactose residue with an alpha (1,3) linkage to a subterminal galactose has been cloned for mouse (Larsen et al., 1989, Proc. Natl. Acad. Sci. USA, 86:8227–8231), ox (Joziasse et al., 1989, J. Biol. Chem. 264:14290–14297), and pig (see copending U.S. application Ser. No. 08/214,580, entitled "Xenotransplantation Therapies", filed by Mauro S. Sandrin and Ian F. C. McKenzie on Mar. 15, 1994, which is incorporated herein by reference—this application also discloses the cloning of the pig genomic gene encoding the transferase). Any of these cDNAs or genomic DNAs can be used to provide the transferase gene to be transduced into target tumor cells as discussed above.

The construction of retroviral vectors directing the expression of such a galactose alpha (1,3) galactosyl transferase can be accomplished by methods well known to those of skill in the art (see above). Such retroviral vectors can be used to transfect packaging cells to yield producer cells providing RVVPs that direct the expression of the transferase enzyme in cells transduced by the vector particles. Target tumor cells transduced with such RVVPs will express galactose alpha (1,3) galactosyl epitopes and will consequently be destroyed by the humoral immune system of a human or Old World primate patient.

Recent in vivo studies have demonstrated that procedures involving the implantation of producer cells into rat solid tumors can effectively deliver RVVPs to adjacent cells (Culver et al., 1992). In one variation of such procedures, producer cells are engineered to express the herpes simplex virus thymidine kinase (HSVTK) gene. Treatment of a patient with ganciclovir post-implantation will kill the HSVTK expressing producer cells as well as any immediately surrounding cells, which, in such procedures, will be tumor cells.

In related studies, producer cells injected into the brain of rats or monkeys were shown to survive for approximately 15 days without proliferating (Widner and Brundin, 1988). The survival of xenogeneic producer cells in the primate brain is not surprising considering that the brain is an immunoprivileged site relative to complement activity and therefore, hyperacute rejection (HAR) commonly associated with xenotransplants into primates does not occur. HAR of xenografts in primates normally occurs within minutes of transplantation due to the activation of the classical complement pathway by preexisting antibodies to alpha-galactosyl epitopes found on the surface of mammalian cells excluding man, apes and Old World monkeys.

The inability to transplant producer cells into non-immunoprivileged sites greatly reduces the conditions under which gene therapy procedures involving the implantation of producer cells into a patient may be carried out. Transient inhibition of RVVP inactivation in accordance with the methods of the present invention that can be carried out transiently (e.g., the administration of IMs) will, in addition to protecting RVVPs, temporarily prevent hyperacute rejection of xenogeneic retroviral producer cells implanted in non-immunoprivileged sites, allowing the producer cells to survive until complement activity rebounds or until the producer cells are eliminated through cellular mechanisms. of course, the other protected PCs of the invention can also be implanted in a patient and will be resistant to hyperacute rejection (this implantation procedure is less preferred because it lacks the extra safety which, as discussed below, is provided by transient inhibition). Concomitantly, in accordance with the invention, the RVVPs liberated from the implanted protected producer cells will be also be protected from inactivation.

Although producer cells and RVVPs (in the absence of replication competent virus) have not been shown to be toxic or pathologic in primates, transient blockade of the activation of complement by producer cells in accordance with those aspects of the invention in which it occurs, i.e., in protected PCs that are not crPCs, provides an additional safety mechanism for the use of implanted producer cells to effect gene therapy; when complement inhibition ceases, producer cells and RVVPs will be eliminated.

In terms of clinical practice, the methods of the present invention will have broad therapeutic utility in facilitating the treatment of a wide range of inherited and acquired diseases and medical conditions including, without limitation, hematologic diseases, cardiopulmonary diseases, endocrinological diseases, immunological diseases, neoplasias, and the like.

Without intending to limit it in any manner, the present invention will be more fully described by the following examples.

EXAMPLES

Materials and Methods

Retrovirus Titer Assay. The retroviral vector pLXSN (Miller and Buttimore, 1986), containing the neomycin resistance gene for selection, was utilized to examine the ability of type C retrovirus to survive in human serum. Retroviral particles were generated from the amphotropic packaging cell line PA317 (ATCC designation CRL 9078) which contains the amphotropic murine leukemia virus gag, pol and env genes (Miller and Buttimore, 1986) by transfection with pLXSN.

Transfectants were pooled and a 24 hour supernatant was harvested from the cells at 90% confluency. The ecotropic RVVP stock was used to infect the amphotropic packaging cell line PA317. These cells were then also selected in DMEM with FCS and G418, following which an RVVP stock was collected from pooled transductants in the same medium without G418 (referred to hereinafter as D10).

RVVP samples were assayed for titer of infectious RVVPs on NIH/3T3 cells (ATCC designation CCL 163). $2.5 \times 10^4$ cells were plated per well in 6-well plates with 2 ml of DMEM containing 10% fetal bovine serum (D10). The medium in each well was replaced with 2 ml of D10 containing 8 $\mu$g/ml of polybrene and retroviral particles were added. Ten-fold dilutions were made from the original well and plates were incubated for 24 h at 37° C. Medium was removed and 2 ml of D10 containing 500 $\mu$g/ml of G418 (active weight) was added. The cells were maintained under selection for 7 days with 2 changes of medium during this period. Finally, medium was removed and colonies were stained with methylene blue saturated methanol for 15 min. followed by a brief rinse in water. Wells containing less than 100 colonies were counted to determine titers.

Retrovirus Killincr Assav in Primate Sera. Retroviral vector particles, including those from PA317 or PA317/H- transferase cells, (approximately 500 CFU) were incubated for 30 min. at 37° C. in 100 μl of 40% primate sera diluted in Hank's balanced salt solution (HESS) and subsequently titered on NIH/3T3 cells to assess retrovirus survival as described above. The different primate sera included human (Diamedix, Cambridge, Mass.), chimpanzee (Southwest Foundation for Research, San Antonio, Tex.), baboon, squirrel monkey, owl monkey and tamarin (all from the New England Regional Primate Research Center, Southborough, Mass.). Data were calculated as percent retrovirus survival in the various sera relative to the number of input CFU (determined by incubation of virus in 40% heat inactivated human serum). In experiments examining the ability to block inactivation of retroviral particles, human serum was preincubated with galactose α1-3 galactose (Galα1-3Gal; Dextra Laboratories, Reading, UK), D(+) glucose, D(+) galactose, α-L(−) fucose, maltose or sucrose (all from Sigma Chemical Company, St. Louis, Mo.) for 30 min. at 37° C. prior to the addition of retrovirus. In the anti-αgalactosyl antibody depletion experiments, retroviral particles were preincubated with either anti-agalactosyl antibody (90 μg/ml) or buffer alone (PBS; BioWhittaker, Walkersville, Md.) for 30 min. at 37° C. before the addition of either 40% human serum, 40% human serum depleted of anti-αgalactosyl antibodies or 40% squirrel monkey serum for an additional 30 min. incubation. Retrovirus survival was then assessed as described above.

Retrovirus Isolation/Purification. Transfectants were pooled and a 24 hour supernatant was harvested from the cells at 90% confluency. The ecotropic RVVP stock was used to infect the amphotropic packaging cell line PA317 (ATCC designation CRL 9078). These cells were then also selected in DMEM with FCS and G418, following which an RVVP stock was collected from pooled transductants in the same medium without G418 (referred to hereinafter as D10).

Serial dilutions of RVVP samples were assayed for titer of infectious RVVPs on NIH/3T3 cells (ATCC designation CCL 163). $2.5 \times 10^4$ cells were plated in 2 ml of D10 in wells of 6-well plates. The following day, medium in each well was replaced with 2 ml of D10 containing 8 mg/ml of polybrene. The RVVP sample was then added. Ten-fold or 100-fold serial dilutions were made from the original well by transfer of aliquots to adjacent wells. The plates were then incubated for 24 hours. Medium was then once again replaced with 2 ml of the D10, in this case containing 500 mg/ml of G418 (active).

Selection was accomplished by incubation in the G418 containing D10 for 10 days with 2 changes of medium during this period. Following this selection, medium was removed and surviving colonies were fixed and stained for 15 minutes with a saturated solution of methylene blue in methanol followed by a brief rinse with water.

Retroviral particles were isolated from the amphotropic packaging cell line PA317 via centrifugation. Briefly, a 24 h supernatant was harvested from confluent flasks of transduced PA317 cells. The supernatant was centrifuged at 40,000 ×g in an SW28 rotor for 90 min. Supernatant was removed and the retroviral pellet was resuspended in HBSS. A 24 h supernatant from confluent NIH/3T3 cells was treated similarly as a no virus control for the western blot analysis.

Anti-αGalactosyl Antibody Purification. Anti-αgalactosyl antibodies were purified from human serum using a Galα1-3Gal-polyacrylamide-glass ($B_{di}$-sorbent) column (Syntesome, Munich, Germany). Briefly, 10 ml of human serum was diluted 1:2 in phosphate buffered saline (PBS), pH 7.5, and passed over a 5 ml $B_{di}$-sorbent column three times. The final column flow through was collected as a source of anti-αgalactosyl antibody depleted serum. After washing the column extensively with PBS, antibody was eluted with immunopure IgG elution buffer (Pierce, Rockford, Ill.) and immediately neutralized by adding 1.0M Tris, pH 8, to a final concentration of 0.1M. Fractions containing protein were combined and dialyzed against PBS overnight.

Enzyme-Linked Immunosorbent Assay (ELISA). Capture ELISAs were performed using flat-bottom 96-well microtitre plates. The plates were coated for 1 h with Fab generated from an anti-gp70 mAb (purified from MuLV gp70 hybridoma 715; NIH AIDS Research and Reference Reagent Program, Rockville, Md.) in 0.1M sodium carbonate buffer, pH 9.6. After blocking the plates in Tris buffered saline (TBS; 20 mM Tris, pH 7.5, 150 mM NaCl) containing 1% BSA for 2 h, undiluted PA317/LXSN viral supernatant was added and incubated for 30 min. In the next step, serially diluted purified anti-αgalactosyl antibody (starting at 70 αg/ml) or biotinylated GS-$IB_4$ lectin (starting at 20 μg/ml; E Y Laboratories, San Mateo, Calif.) was added for a 30 min. incubation. HRP-conjugated Streptavidin or HRP-conjugated anti-human IgG antibody (Zymed Laboratory, San Francisco, Calif.) was added for 30 min and plates were developed using peroxidase substrate. All incubations were performed at 37° C. and plates were washed between steps with TBS containing 1% BSA. Absorbance values were measured on a Bio-Rad microplate reader (Hercules, Calif.) at 492 nm and corrected for background absorbance using identically treated wells in the absence of retroviral particles.

Western Blot Analysis. Purified retrovirus in HBSS or mock purified supernatant was size fractionated via SDS-PAGE on a 12% gel. Proteins were transferred to nitrocellulose and the membrane was incubated for 1 h in blocking solution (500 mM NaCl, 35 mM Tris pH 7.4, 0.5 mM $CaCl_2$, 10% Carnation nonfat dry milk and 0.2% Tween-20). Identical blots were incubated for 45 min in 5 μg/ml of HRP-conjugated GS-$IB_4$ lectin, 5 μg/ml HRP-conjugated UEA lectin (Sigma, St. Louis, Mo.) or a 1:1000 dilution of anti-gp70 mAb (provided by Dr. James Mason, Alexion Pharmaceuticals Inc.), all diluted in fresh blocking solution. Blots were washed 2× with antibody wash solution (500 mM NaCl, 35 mM Tris pH 7.4, 0.5 mM $CaCl_2$, 0.1% SDS, 1.0% NP-40 and 0.5% deoxycholic acid). The blot previously reacted with anti-gp70 mAb was incubated for 20 min in fresh blocking solution containing 1.0% NP-40 and HRP-conjugated goat anti-rat IgG (1:2000 dilution) (Zymed Laboratory, San Francisco, Calif.). Finally, blots were washed 2× in antibody wash solution, incubated for 1 min in ECL western blot reagent and exposed to ECL Hyperfilm (Amersham, Arlington Heights, Ill.).

Generation and Analysis of H-Transferase/PA317 Transductants. The full-length human H-transferase cDNA was obtained by PCR amplification of reverse transcribed cDNA from human epitheloid carcinoma cells using primers that flanked the start and stop codons of the molecule. The cDNA was subcloned as an EcoR1 fragment into the pLXSN retroviral vector. Amphotropic retroviral particles were produced through the intermediate ecotropic packaging cell line GPE86 (Markowitz et al.1988). Briefly, GPE86 cells were transfected with pLXSN containing H-transferase or pLXSN alone using the calcium phosphate method (Ausubel et al. 1991) followed by selection in D10 medium containing 500 μg/ml G418. Transfectants were pooled and a 24 h supernatant was harvested from cells at 90% confluency. The ecotropic virus stock was used to transduce the amphotropic packaging cell line PA317 which was also selected as a pool in G418. The transduced PA317 cells were screened for surface expression of the agalactosyl epitope or H-antigen by fluorescence staining using purified anti-αgalactosyl Ab, GS-IB$_4$ lectin or UEA lectin. Cell surface staining was performed on $2.5 \times 10^5$ cells with 20 μg/ml of anti-αgalactosyl antibody or 10 μg/ml of FITC-conjugate GS-IB$_4$ or FITC-conjugated UEA in 1× PBS with 2% fetal bovine serum. FITC-conjugated goat anti-human IgG (Zymed Laboratories, South San Francisco, Calif.) was used as a secondary antibody for cells incubated with anti-αgalactosyl Ab. Fluorescence was measured by FACS using a Becton-Dickenson FACSort (Becton-Dickenson Immunocytometry Systems, San Jose, Calif.).

Complement-Mediated Dye Release Assay. Complement-mediated damage (killing) of PA317 cells transduced with H-transferase or the pLXSN vector alone was assessed by measuring the release of the cytoplasmic indicator dye, Calcein AM (Molecular Probes, Inc., Eugene, Oreg.) following exposure to human serum. PA317 cells were grown to confluency in 96-well plates, washed 2× with Hank's balanced salt solution (HBSS) containing 1% BSA and incubated with 10 μM Calcein AM at 37° C. for 30 min. Cells were again washed 2× before the addition of human serum for a 30 min incubation at 37° C. Dye release was measured on a Millipore Cytofluor 2350 plate reader (excitation, 490 nm; emission, 530 nm). Dye retained, represented as percent cell survival, was calculated from the percent dye released relative to total cell associated dye (determined from dye released from cells treated with 1% SDS). Dye release from cells not subjected to serum treatment allowed the determination of background fluorescence and non-specific dye release. In the anti-αgalactosyl antibody depletion experiment, Calcein AM loaded cells were incubated for 30 min at 37° C. with either anti-αgalactosyl antibody (90 μg/ml) or buffer alone (PBS) and unbound antibody was removed with 2 washes in HBSS containing 1% BSA. Cells were then exposed to either 20% human serum, 20% anti-αgalactosyl antibody depleted serum or 20% squirrel monkey serum for 30 min at 37° C. and percent cell survival was determined as described above.

Example 1
Inactivation of LXSN retroviral vector Particles in primate sera.

Figure 1:
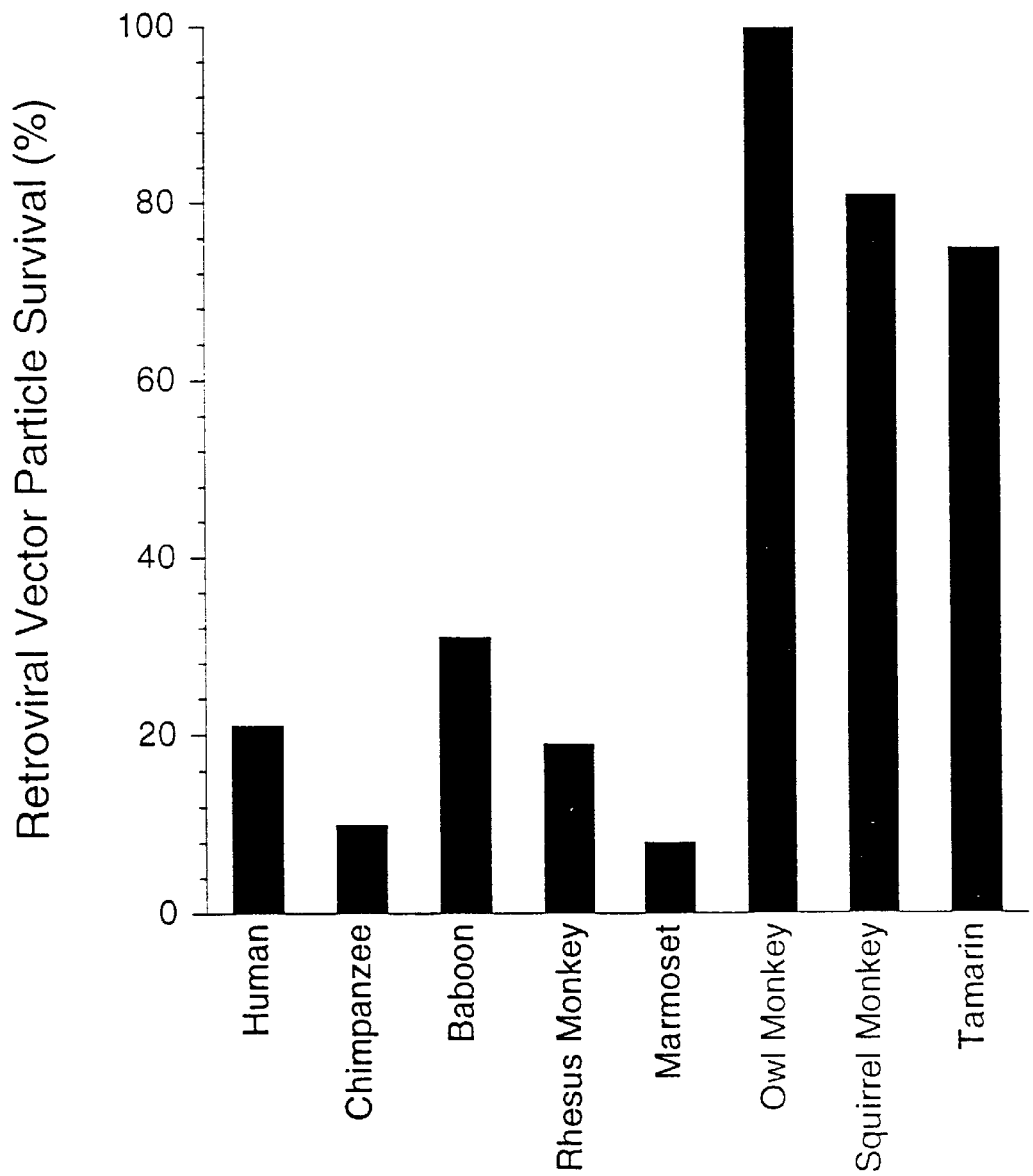
FIG. 1 shows retroviral vector particle survival (i.e., retention of ability to transduce target cells) in serum from various primates as indicated. These experiments were carried out using LXSN RVVPs as described below in the examples.

Previous studies have demonstrated that many types of retroviruses are lysed by human or nonhuman primate sera. Particles of the Moloney murine leukemia virus derived vector LXSN were subjected to treatment as follows. RVVPs were treated with either human serum or sera from Chimpanzee, Baboon, Rhesus Monkey, Marmoset, Owl Monkey, Squirrel Monkey, and Tamarin. Chimpanzee, Baboon, and Rhesus Monkey are Old World primates; Marmoset, Owl Monkey, Squirrel Monkey, and Tamarin are New World primates. The activity of the RVVPs in transducing NIH/3T3 cells was then determined. Percent survival was calculated relative to particles incubated in heat inactivated serum or in the absence of serum. As shown in FIG. 1, the results obtained in these studies indicate that, while human serum and all Old World primate sera tested provide significant viral (RVVP) inactivation, most New World primate sera tested provide very little viral inactivation. The significant inactivation levels obtained with Marmoset serum indicate that this serum is not typical of New World primate sera, as killing in this serum does not appear to be mediated via anti-alpha (1,3) galatosyl antibodies.

Figure 2:
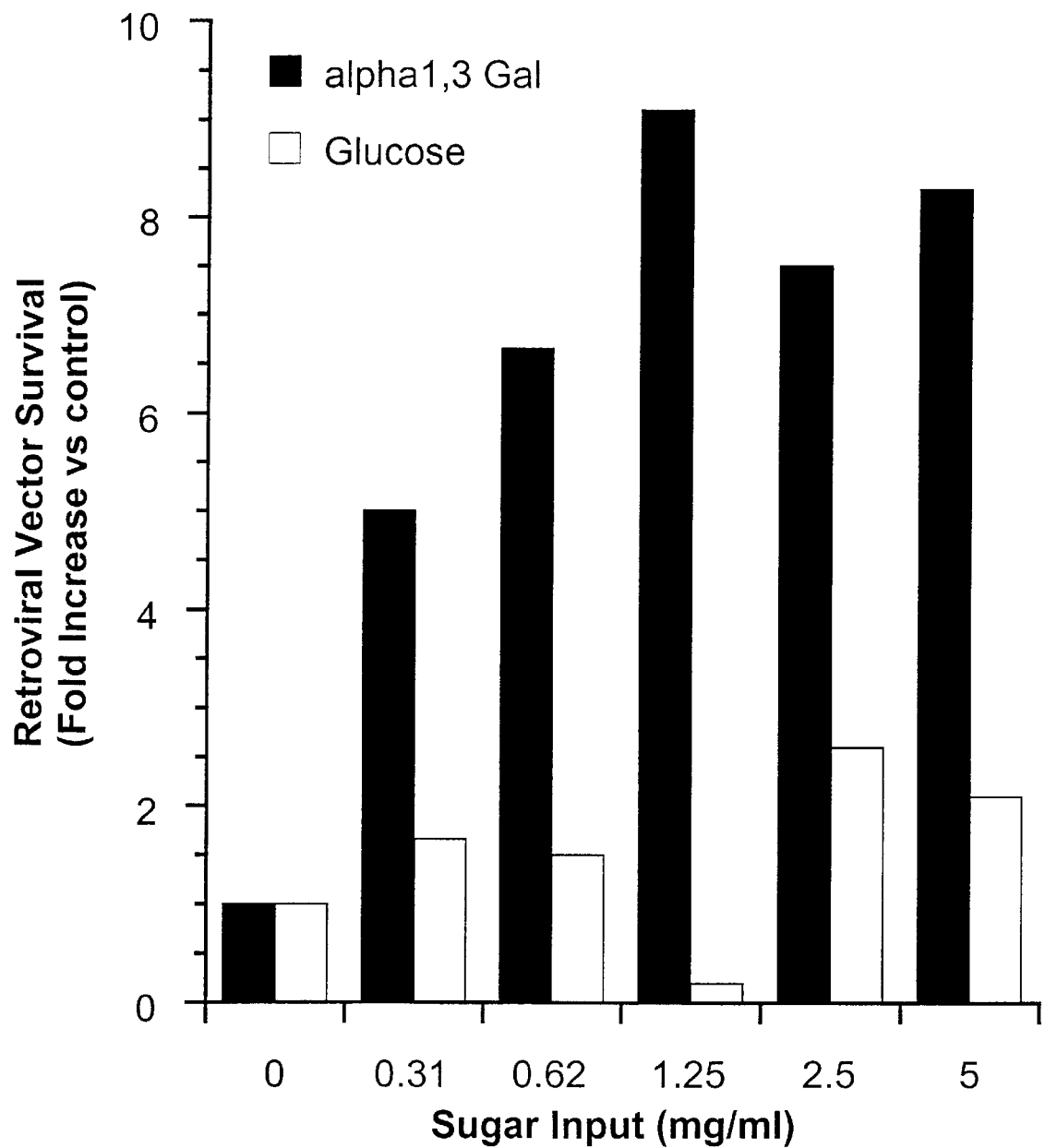
FIG. 2 shows retroviral vector particle survival in human serum in the presence of glucose or galactose alpha (1,3) galactose. These experiments were carried out using LXSN RVVPs as described below in the examples.

Example 2
Inactivation of LXSN retroviral vector particles in the presence of added sugars LXSN retroviral vector particles were prepared as described above. Aliquots of a 40% solution of human serum in HBSS were then incubated for 15 minutes at room temperature with added sugars. The sugars added were D-glucose (Mallinckrodt, Paris, Ky.) and galactose alpha-1,3 galactose (Dextra Laboratories, Reading, England), and were added at concentrations of 0.3125, 0.625, 1.25, 2.5, and 5 mg/ml. Samples without added sugars were tested in parallel as controls. After incubation, the LXSN particles were titered on NIH/3T3 cells as described above. The results of these titrations were calculated as fold increase in retroviral vector particle survival relative to the control samples, and are set forth in FIG. 2. These results demonstrate that galactose alpha-1,3 galactose, but not glucose, substantially reduces the inactivation of the retroviral vector particles by human serum at all concentrations used.

Example 3
Flow cytometric analysis for galactose alpha (1,3) galactosyl epitopes on mammalian cell lines To identify mammalian cell lines lacking the galactose alpha (1,3) galactosyl epitope, several cell lines were screened by flow cytometry using an FITC-conjugated lectin (GS-IB4; E.Y. Laboratories, San Mateo, Calif.) which is specific for the galactose alpha (1,3) galactosyl epitope. $1 \times 10^6$ cells derived from various cell lines were collected after trypsinization, washed once in 400 ul of HBSS, and resuspended in 100 ul of HBSS supplemented with a) no addition; b) 10 ug/ml of FITC-conjugated UEA lectin (E.Y. Laboratories, San Mateo, Calif.) for the detection of the H-epitope (alpha-(1,2) fucosyl epitope); or c) 10 ug/ml of FITC-conjugated GS-IB4 lectin. The cells were incubated on ice in the dark for 30 minutes and then pelleted by centrifugation, washed in 400 ul HBSS, and then resuspended in 500 ul of HBSS for flow cytometric analysis using a Becton-Dickenson FACSort (Becton Dickenson Immunocytometry Systems, San Jose, Calif.). FIGS. 7 and 9 demonstrates that murine PA317 cells and hamster CHO LEC8 cells were strongly positive for GS-IB4 binding whereas human HeLa cells (ATCC designation CCL 2), hamster CHO-DG44 cells (obtained from Dr. L. Chasin, Columbia University, New York.), and hamster BHK-21 cells (ATCC designation CCL-10) were negative for GS-IB4 staining indicating their lack of galactose alpha (1,3) galactosyl epitopes. Such negative for staining non-human, non Old World primate cells are preferred for use in this aspect of the present invention, while human cells, Old World primate cells, and positively staining cells are not preferred. As expected, human HeLa cells were positive for UEA staining, indicating their expression of the human H-epitope.

Example 4
Transient expression of RVVPs in CHO-DG44 cells

Cells from the CHO-DG44 cell line were plated on P100 tissue culture dishes at approximately 25% confluence in appropriate growth media (F12 supplemented with 10% FBS and hypoxanthine, glycine, and thymidine). The following day, the media was changed to DMEM with 10% heat-inactivated FBS (D10) and the cells were transfected with CaPO$_4$ with 25 ug each of the following plasmids: Gag-Pol-gpt (Markowitz et. al., 1988); LXSN, and CAE or CXE (Morgan et. al., 1993). CaPO$_4$ precipitates were washed from cells the following day using PBS and fresh Ham's F12 media was added. Twenty-four hours post-wash, fresh media was again added and vector particle containing media (viral supernatants) was collected and pooled at 48 and 72 hours post-wash. Viral supernatants were cleared of cells and debris by centrifugation in a clinical centrifuge for 5 minutes at 1000 xg and cleared viral supernatants were concentrated from 20 mls to 0.6 mls using Centraprep 100 column (Amicon, Beverly, Mass.).

Example 5

Complement resistance of RVVPs produced transiently in CHO-DG44 cells

Human serum collected and pooled from numerous donors was obtained from either Sigma (St. Louis, Mo.) or Diamedix (Cambridge, Mass.). Lyophilized serum was reconstituted in cold sterile water to its original volume and stored on ice to provide active complement, while a portion of the same serum was treated to heat-inactivate (HI) serum complement by incubation at 56° C. for 30 minutes. The active and HI sera were then transferred to 1.5 ml eppendorf tubes in 50 ul aliquots. All viral supernatants were assayed in duplicate or triplicate as follows. Viral supernatants (50 ul) were added to the eppendorf tubes containing active or HI human sera to give a final concentration of 50% serum. The samples were incubated for 30 to 45 minutes at 37° C. The samples were then titered onto the appropriate indicator cells to assess survival of the RVVPs. Mink lung fibroblasts (ATCC designation CCL 64) were used to assess survivability of the xenotropic viral particles whereas NIH/3T3 cells were used to quantify survival of the amphotrophic viral particles. $2.5 \times 10^4$ indicator cells/well were plated in 6-well tissue culture plates containing 2 mls of D10 supplemented with 8 ug/ml of polybrene. Titers were performed by dilution of the entire volume (100 ul) into the first well. After vigorous mixing, 200 ul from the first well was transferred to the second well and then 200 ul was transferred from the second to the third well. The following day and 5 days later, media was changed to fresh D10 containing either 600 or 1200 ug/ml of active G418 for NIH/3T3 or mink cells, respectively. Neomycin resistant colonies were scored 7 to 10 days post-selection by methylene blue staining. The percent survival was determined by dividing the average titer in the presence of active serum times 100 divided by the average titer in the presence of HI serum. As shown in FIG. [4], transiently expressed vector particles from CHO-DG44 cells containing either amphotrophic or xenotrophic envelopes showed approximately 50% survival compared with RVVPs generated from murine GPE86 producer cells, which showed less than 2% survival.

Example 6

Generation of stable pre-packaging and packaging cell lines from CHO-DG44 and BHK-21 cell lines CHO-DG44 and BHK-21 cells were plated onto P60 tissue culture dishes and co-transfected by the $CaPO_4$ method with approximately a 5-fold molar excess of plasmid Gag-Pol-gpt versus the puromycin selection plasmid CPURO (see copending U.S. patent applications Ser. Nos. 08/181,335 and 08/182,612, both entitled "Retroviral Vector Particles for Transducing Non-Proliferating Cells" and both filed Jan. 14, 1994.) which imparts resistance to the antibiotic puromycin. The cells were grown for 10 to 14 days in 6–8 ug/ml of puromycin (Sigma, St. Louis, Mo.), and cloned using cloning cylinders. Clones were expanded in 6-well dishes in non-selective media. Culture supernatants were assayed for reverse transcriptase activity (RT) (Markowitz et. al. 1988) and some RT-positive clones were evaluated further for vector particle production following transient transfection of the env gene and pLXSN by using viral titer assays on NIH/3T3 cells.

The highest titer CHO-DG44 and BHK-21 pre-packaging cell lines obtained in this fashion are plated onto tissue culture plates and cotransfected with envelope expression plasmids CAE or CXE and the selectable marker plasmid pTH which confers resistance to hygromycin (see copending U.S. patent applications Ser. Nos. 08/181,335 and 08/182,612, both entitled "Retroviral Vector Particles for Transducing Non-Proliferating Cells" and both filed Jan. 14, 1994, both of which are incorporated herein by reference). Hygromycin-resistant clones are isolated as described above and then transfected with a retroviral vector plasmid containing a gene of therapeutic interest to generate cells that are expanded to produce cultures containing packaging lines, or with plasmid pLXSN to generate cells that are expanded to produce cultures of a test packaging cell line. RVVPs collected in viral supernatants from stable CHO-DG44 and BHK-21 packaging cells are resistant to human serum and complement-mediated virolysis when compared to RVVPs packaged in murine NIH 3T3 derived packaging cell lines such as PA317 or GPE86.

Example 7

Generation of complement resistant RVVPs from packaging cells treated with glycosylation inhibitors In order to prepare galactose alpha (1,3) galactosyl epitope deficient retroviral particle producer cells, LXSN transduced murine PA317 producer cells were cultured in D10 medium, washed twice with 10 ml of HBSS and then incubated in 18 ml of fresh D10 medium containing either: 1) no glycosylation inhibitor; 2) 200 ug/ml deoxymannojirimycin; 3) 5 ug/ml swainsonine; or 4) 200 ug/ml castanospermine (all inhibitors obtained from Oxford Glycosystems, Rosedale, N.Y.).

The PA317 cells were then incubated with inhibitors for 2 hours, at which time the media were removed and replaced with 18 ml of fresh D10 medium containing the same concentrations of the same inhibitors. The cultures were then incubated for about 24 hours, at which time the media (containing RVVPs) were collected. Duplicate aliquots of the RVVPs so obtained were then challenged with 40% human serum or with 40% HI human serum as a control. The RVVPs obtained from the cells cultured in the presence of castanospermine showed a considerable reduction in susceptibility to complement mediated inactivation (50% to 70% survival compared to essentially no survival for the RVVPs obtained from producer cells cultured in the absence of inhibitors), i.e., they were crRVVPs.

Further Discussion of Examples 1–7 and Additional Examples

Figure 3:
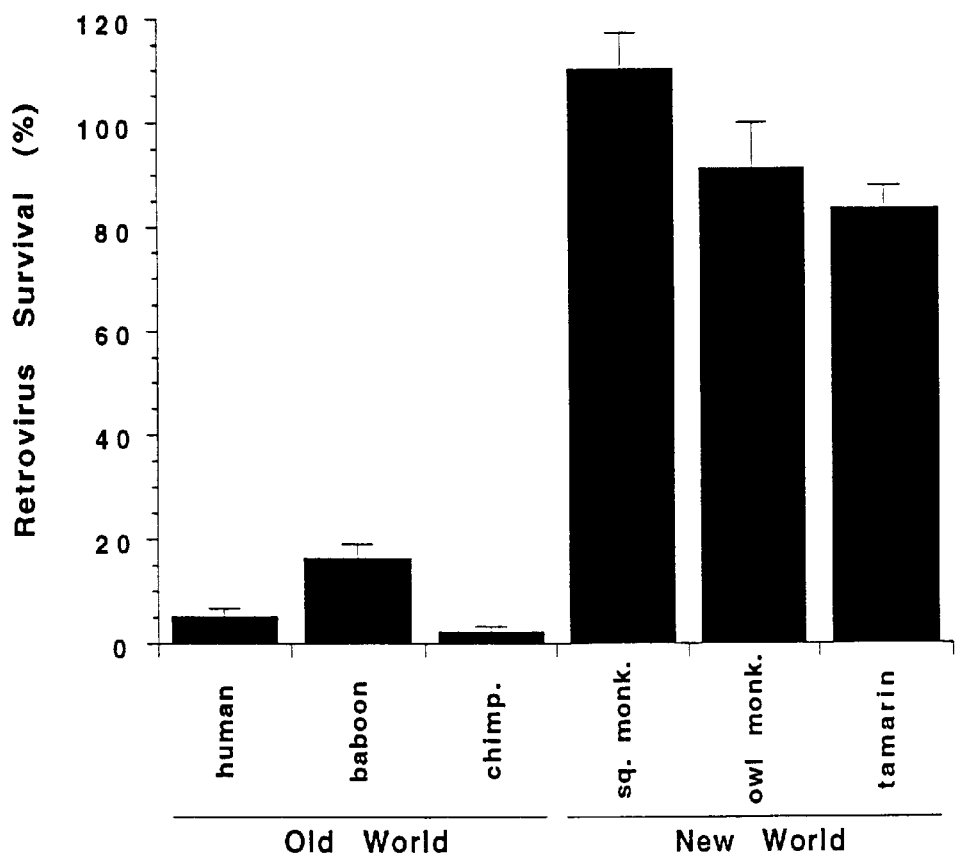
FIG. 3 shows Retrovirus survival in Old World versus New World primate sera. Amphotropic retroviral particles were incubated in sera from Old World primate species including human, baboon or chimpanzee (chimp.) or with sera from New World primate species including squirrel monkey (sq. monk.), owl monkey (owl monk.)or tamarin. Following exposure to 40% serum, retrovirus was titered on NIH/3T3 cells to assess survival. Bars represent the percentage of infectious particles remaining relative to the number of input virus (determined from survival in 40% heat inactivated human serum). Data represent duplicate determinations of a single experiment, one of three so performed. Error bars denote standard error of the mean.

Survival of Retrovirus in Sera of Old and New World Primates. Previous studies have demonstrated that many type C retroviruses are effectively inactivated in Old World primate sera but not sera from various other mammalian species (Welsh et al.1975; Welsh et al. 1976; Banapour et al. 1986; Cornetta et al.1990). Additionally, recent studies have shown that Old World, but not New World, primates produce anti-αgalactosyl antibody (Galili et al. 1987; Galili et al. 1988b). To investigate the potential role of this antibody in the inactivation of type C retroviruses, retroviral particles containing the murine leukemia virus derived amphotropic envelope were incubated in sera from various Old World (human, baboon and chimpanzee) and New World (squirrel monkey, owl monkey and tamarin) primate species. All primate sera were shown to have similar functional complement levels in a classical pathway-mediated chicken erythrocyte hemolytic assay (data not shown). Sera from Old World primate species effectively inactivated the retrovirus with a mean survival of 7.5% (FIG. 3). In contrast, the retrovirus was resistant to inactivation in New World primate sera with a mean survival of 95%. The survival of amphotropic retroviral particles in New World, but not Old World, primate sera parallels the presence of anti-αgalactosyl Ab, suggesting that this natural antibody may play a role in complement-mediated inactivation of type C retroviruses.

Galα1-3Gal Blocks Retrovirus Inactivation in Human Serum. Synthetic galactose α1-3 galactose (Galα1-3Gal) has been shown to specifically bind anti-αgalactosyl antibody (Galili, 1993). Furthermore, it has been demonstrated that this carbohydrate serves as an effective inhibitor of anti-αgalactosyl Ab-initiated complement lysis of cells expressing the αgalactosyl epitope (Neethling et al. 1994). In experiments disclosed herein, Galα1-3Gal prior to the addition of retroviral particles. Preincubation of human serum with Galα1-3Gal successfully inhibited retrovirus inactivation in a dose-dependent manner (FIG. 4). The addition of 5 mg/ml Galα1-3Gal completely blocked complement-mediated virolysis. In contrast, D(+) glucose, α-L(−) fucose, maltose or sucrose added to the serum at a concentration of 5 mg/ml did not affect retrovirus survival. Preincubation of serum with D(+) galactose (5 mg/ml), which has been shown to block anti-αgalactosyl antibody reactivity (Galili et al. 1984; Sandrin et al. 1993; Vaughan et al.1994), inhibited approximately 25% of retrovirus inactivation. Similar results were obtained when retroviral particles were challenged with serum from other Old World primates including baboon and chimpanzee. Taken together, these data demonstrate the unexpected finding that anti-αgalactosyl antibody plays a major, predominant role in the complement-mediated inactivation of murine derived type C retroviral particles in human serum.

Contribution of Anti-αgalactosyl antibody to Retrovirus Inactivation by Human Serum. Previous studies have described type C murine retrovirus inactivation by human serum complement as an Ab-independent event initiated by the direct binding of C1q to the retroviral envelope (Bartholomew and Esser, 1980; Bartholomew et al. 1978; Cooper et al. 1976; Welsh et al. 1976). We have now demonstrated that complement activation on the surface of type C retroviral particles is predominantly initiated through an Ab-dependent mechanism involving natural antibody directed against the αgalactosyl epitope. To determine the direct contribution of anti-αgalactosyl antibody to retrovirus inactivation, human serum was selectively depleted of this antibody prior to incubation with either PA317 retroviral particle producer cells or retroviral particles liberated from these cells. It has been shown that depletion of anti-αgalactosyl natural antibody from human serum eliminates the ability of that serum to mediate killing of cells expressing the agalactosyl epitope (Vaughan et al. 1994). Following anti-αgalactosyl antibody depletion, the absorbed serum retained normal levels of complement activity as determined in a classical complement-mediated chicken erythrocyte hemolytic assay (data not shown). PA317 cells producing LXSN amphotropic retroviral particles were loaded with the cytoplasmic dye Calcein AM and exposed to human serum or anti-αgalactosyl antibody depleted serum. While only 30% of PA317 cells survived exposure to human serum, 85% of cells survived in the depleted human serum (FIG. 5, Panel A). Similarly, 85% of cells incubated with squirrel monkey serum, which does not contain anti-αgalactosyl Ab, survived indicating that anti-αgalactosyl antibody had been effectively removed from the depleted human serum. Conversely, addition of the purified anti-αgalactosyl antibody to squirrel monkey serum resulted in killing of the PA317 cells. These data demonstrate that anti-αgalactosyl antibody plays a critical role in the activation of complement on the surface of PA317 retroviral particle producer cells.

In order to determine whether anti-αgalactosyl antibody also plays a major role in the killing of retroviral particles generated from the PA317 producer cells, retrovirus was incubated with either human serum or anti-αgalactosyl antibody depleted human serum. Only 5% of input retrovirus survived in human serum while retrovirus survival in depleted serum was 100% (FIG. 5, Panel B). As was shown for the PA317 cells, incubation of retroviral particles with untreated squirrel monkey serum had no affect on retrovirus survival while squirrel monkey serum in the presence of purified anti-αgalactosyl antibody effectively inactivated the retrovirus. The inability to achieve 100% retrovirus inactivation in squirrel monkey serum could reflect insufficient concentrations of the anti-αgalactosyl Ab. Although the final concentration of purified anti-αgalactosyl antibody in the squirrel monkey serum (approximately 50 μg/ml) was similar to that previously reported in human serum (Galili et al. 1984), the binding of anti-αgalactosyl antibody to αgalactosyl epitopes associated with squirrel monkey serum proteins may decrease antibody available for binding to the retroviral envelope. Taken together, these data indicate that type C amphotropic retroviral particle inactivation by human serum complement is initiated by anti-αgalactosyl natural Ab.

Expression of the αGalactosyl Epitope on the Viral Envelope. We have shown that blockade or removal of anti-αgalactosyl antibody in human serum prevents amphotropic retroviral particle inactivation. To confirm the presence of the αgalactosyl epitope on the surface of the retroviral envelope, a capture ELISA was performed. Plates were coated with Fab directed against the retroviral envelope protein gp70 and retroviral particles were captured from supernatants of amphotropic producer cells. Plates were then exposed to affinity purified anti-αgalactosyl antibody or the lectin *Griffonia simplicifolia* (GS)-IB$_4$. This lectin has been shown to specifically interact with the αgalactosyl epitope (Wood et al. 1979; Repik et al. 1994). Anti-αgalactosyl antibody and GS-IB$_4$ lectin bound to the retrovirus in a dose-dependent fashion (FIG. 6). These data establish that the agalactosyl epitope is expressed on the retroviral surface and that this epitope is recognized by anti-αgalactosyl natural Ab.

Association of the αGalactosyl Epitope with the Viral gp70 Envelope Protein. A recent study has demonstrated that the αagalactosyl epitope is associated with the envelope glycoproteins E1 and E2 of the eastern equine encephalitis virus, a DNA virus (Repik et al. 1994). We have shown that the αgalactosyl epitope is present on the surface of amphotropic retroviral particles. To determine if the αgalactosyl moiety on the retroviral surface is associated with a particular envelope protein, western blot analysis was performed. Protein extracts from purified retroviral particles were assayed for reactivity with GS-IB$_4$ lectin, Ulex europaeus agglutinin type I (UEA) lectin or anti-gp70 mAb. The GS-IB$_4$ lectin specifically recognized a molecule at approximately 70 kDa. This molecular weight corresponds with that of the murine leukemia virus major envelope glycoprotein, gp70. The anti-gp70 mAb recognized a molecule at the same position on the blot indicating that the agalactosyl epitope is associated with gp70. UEA lectin, which recognizes a different glycosidic structure (see below) did not react with gp70 or any other molecule on the blot. Purified supernatants from NIH/3T3 cells did not react with lectins or the mAb confirming that the 70 kDa band was of viral origin. These results demonstrate that the αgalactosyl epitope expressed on the surface of amphotropic retroviral particles is associated with the envelope glycoprotein gp70.

Downregulation of the αGalactosyl Epitope on PA317 Producer Cells Results in the Production of Serum-Resistant Retrovirus.

We have recently shown that overexpression of α1-2fucosyl transferase (H-transferase) in porcine cells (LLC-PK1) drastically reduces the expression of the agalactosyl epitope due to substrate competition between the H-transferase and α(1-3) galactosyl transferase enzymes (see copending U.S. patent application Ser. No. 08/278,282, entitled "Methods for Reducing Hyperacute Rejection of Xenografts", filed Jul. 21, 1994 in the names of Mauro S. Sandrin, William L. Fodor, Russell P. Rother, Stephen P. Squinto, and Ian F. C. McKenzie, the relevant portions of which are incorporated herein by reference.

Furthermore, downregulation of the αgalactosyl epitope on these cells resulted in decreased sensitivity to human serum killing. The H-transferase enzyme transfers a fucose residue to an N-acetyl lactosamine acceptor to generate fucosylated N-acetyl lactosamine (H antigen), a glycosidic structure that is not recognized by anti-αgalactosyl antibody (Larsen et al. 1990a).

To investigate the effect of αgalactosyl epitope downregulation on the serum sensitivity of retrovirus, H-transferase was expressed in the PA317 retroviral particle producer cells. PA317 producer cells were transduced with H-transferase (PA317/H-transferase) or the pLXSN vector alone (PA317/LXSN) and selected as pools in G418. Transduced cells were reacted with $GS-IB_4$ lectin, UEA lectin (which recognizes the H antigen) or anti-αgalactosyl antibody and analyzed by FACS. PA317/LXSN cells expressed high levels of the αgalactosyl epitope, while expression of H antigen in these cells was low (FIG. 7, panel A).

Conversely, PA317/H-transferase cells showed an increase in H antigen expression while αgalactosyl epitope expression was reduced by more than 90% (FIG. 7, panel B) Similarly, binding of purified anti-αgalactosyl antibody to the PA317/H-transferase producer cells was greatly reduced (FIG. 7, panel C). These results show that expression of H-transferase in the PA317 producer cells drastically reduces agalactosyl epitope expression.

In an attempt to correlate αgalactosyl epitope expression with human serum killing, the sensitivity of both the PA317/ H-transferase producer cells and the retroviral particles liberated from these cells was investigated. The producer cells were incubated with human serum and their survival assessed in a dye release assay. PA317/H-transferase cells showed a marked increase in survival relative to PA317/ LXSN cells following exposure to 10 or 20% human serum (FIG. 8, panel A). These results indicate that the level of αgalactosyl epitope expression inversely correlates with the survival of PA317 retroviral particle producer cells in human serum.

Concomitantly, 56% of retrovirus generated from the PA317/H-transferase producer cells survived exposure to human serum while only 1% of retrovirus from the PA317/ LXSN producer cells survived (FIG. 8, panel B). These data indicate that downregulation of αgalactosyl epitope expression on producer cells results in the release of retroviral particles that are resistant to inactivation by human serum complement.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

Although preferred and other embodiments of the invention have been described herein, further embodiments may be perceived by those skilled in the art without departing from the scope of the invention as defined by the following claims.

REFERENCES

Aaronson, S. A. and Todaro, G. J.: Transformation and virus growth by murine sarcoma viruses in human cells. Nature 225 (1970) 458–459.

Almeida, I. C., Milani, S. R., Gorin, A. J. and Travoassos, L. R.: Complement mediated lysis of *Trypanosoma cruzi* tryptomastigotes by human anti α-galactosyl antibodies. J.Immunol. 146 (1991) 2394–2400.

Anderson, 1992. *Science* 256, pp. 808–813.

Ausubel et al., 1992. *Current Protocols in Molecular Biology*, Wiley Interscience, John Wiley and Sons, New York. Volume 1, Section III, units 9.10.1–9.14.3.

Ausubel, F. M., Brent, R., Kingston, R. E., Moore, D. D., Seidman, J. G., Smith, J. A. and Struhl, K.: Current protocols in molecular biology I. John Wiley & Sons, New York, 1991.

Banapour, B., Sernatinger, J. and Levy, J. A.: The AIDS-associated retrovirus is not sensitive to lysis or inactivation by human serum. Virol. 152 (1986) 268–271.

Barbacid, M., Bolognesi, D. and Aaronson, S. A.: Humans have antibodies capable of recognizing oncoviral glycoproteins: demonstration that these antibodies are formed in response to cellular modification of glycoproteins rather thatn as consequence of exposure to virus. Proc. .Natl.Acad.Sci.USA 77 (1980) 1617–1621.

Bartholomew et al., 1978. *J Exp Med* 147, pp. 844–853.

Bartholomew et al., 1980. Biochemistry 19, pp. 2847–2853.

Bartholomew, R. M. and Esser, A. F.: Mechanism of antibody-independent activation of the first component of complement (C1) on retrovirus membranes. Biochem. 19 (1980) 2847–2853.

Bartholomew, R. M., Esser, A. F. and Muller-Eberhard, H. J.: Lysis of oncornaviruses by human serum: isolation of the viral complement (C1) receptor and identification as p15E. J.Exp.Med. 147 (1978) 844–53.

Boggs, 1990. *Int J Cell Cloning* 8, pp. 80–96.

Boiron, R. R., Bernard, C. and Chuat, J. C.: Replication of mouse sarcoma virus Moloney strain (MSV-N) in human cells. Proc.Amer.Assoc.Cancer Res. 10 (1969) 8.

Brinster et al., 1989. *Proc Natl Acad Sci, USA* 86, pp. 7087–7091.

Capecchi, 1989. *Trends in Genetics* 5(3), pp. 70–76.

Cohen, 1989. *Oligodeoxynucleotides, Antisense Inhibitors of Gene Expression*, CRC Press, Inc., Boca Raton, Fla.

Coligan et al., (eds.), 1992. *Current Protocols in Immunology*, John Wiley & Sons, New York.

Cone and Mulligan, 1984. *Proc Natl Acad Sci, USA* 81, pp. 6349–6353.

Cooper et al., 1976. *J Exp Med* 144, pp. 970–984.

Cooper, N. R., Jensen, F. C., Raymond, M. W. and Oldstone, M. B. A.: Lysis of RNA tumor viruses by human serum: direct antibody-independent triggering of the classical complement pathway. J.Exp.Med. 144 (1976) 970–984.

Cornetta, K., Moen, R. C., Culver, K., Morgan, R. A., McLachlin, J. R., Sturm, S., Selegue, J., London, W., Blaese, R. M. and Anderson, W. F.: Amphotropic murine leukemia retrovirus is not an acute pathogen for primates. Hum.Gene Ther. 1 (1990) 15–30.

Cornetta, K., Morgan, R. A. and Anderson, W. F.: Safety issues related to retroviral-mediated gene transfer in humans. Hum.Gene Ther. 2 (1991) 5–14.

Cosset et al., 1990. *J Virol* 64, pp. 1070–1078.
Culver et al., 1992. *Science* 256, pp. 1550–1552.
Delwart, E. L., Panganiban A. T. N-linked glycosylation and reticuloendotheliosis retrovirus envelope glycoprotein function. Virology 179 (2) (1990) 648–57.
Donahue, R. E., Kessler, S. W., Bodine, D., Goodman, S., Agricola, B., Byrne, E., Raffeld, M., Moen, R., Bacher, J., Zsebo, K. M. and Nienhuis, A. W.: Helper virus induced T cell Lymphoma in nonhuman primates after retroviral mediated gene transfer. J.Exp.Med. 176 (1992) 1125–1135.
Eglitis et al., 1988. *Biotechniques* 6, pp. 608–614.
Eglitis, 1991. *Human Gene Therapy* 2, 195–201.
Eguchi et al., 1991. *Annu Rev Biochem* 60, pp. 631–652.
Famulari, N. G.: Murine leukemia viruses with recombinant env genes: a discussion of their role in leukemogenesis. Curr.Top.Microbiol.Immunol. 103 (1983) 103–108.
Felgner and Rhodes, 1991. *Nature* 349, pp. 351–352.
Frohman and Martin, 1989. *Cell* 56, pp. 145–147.
Galili, U. and Swanson, K.: Gene sequences suggest inactivation of $\alpha$-1,3-galactosyltransferase in catarrhines after the divergence of apes from monkeys. Proc.Natl.Acad.Sci.USA 88 (1991) 7401–7404.
Galili, U., Clark, M. R., Shohet, S. B., Buehler, J. and Macher, B. A.: Evolutionary relationship between the natural anti-Gal antibody and the Gala1-3Gal epitope in primates. Proc.Natl.Acad.Sci.USA 84 (1987) 1369–1373.
Galili, U., Macher, B. A., Buehler, J. and Shohet, S. B.: Human natural anti-$\alpha$-galactosyl IgG. II. The specific recognition of $\alpha$(1-3)-linked galactose residues. J.Exp.Med. 162 (1985) 573–582.
Galili, U., Mandrell, R. E., Hamadeh, R. M., Shohet, S. B. and Griffiss, J. M.: Interaction between human natural anti-$\alpha$galactosyl immunoglobulin G and bacteria of the human flora. Infect.Immun. 56 (1988a) 1730–1737.
Galili, U., Rachmilewitz, E. A., Peleg, A. and Flechner, I.: A unique natural human IgG antibody with anti-$\alpha$-galactosyl specificity. J.Exp.Med. 160 (1984) 1519–1531.
Galili, U., Shohet, S. B., Kobrin, E., Stults, C. L. M. and Macher, B. A.: Man, apes, and Old World monkeys differ from other mammals in the expression of $\alpha$-galactosyl epitopes on nucleated cells. J.Biol.Chem. 263 (1988b) 17755–17762.
Galili, U.: Evolution and pathophysiology of the human natural anti-$\alpha$-galactosyl IgG (anti-Gal) antibody. Springer Semin.Immunopathol. 15 (1993) 155–171.
Galili, U.: The natural anti-Gal antibody, the B-like antigen, and human red cell aging. Blood Cells 14 (1988) 205–220.
Geyer, R., Geyer, H., Stirm, S., Hensmann, G., Schneider, J., Dabrowski, U. and Dabrowski, J.: Major oligosaccharides in the glycoprotein of Friend murine leukemia Virus: structure elucidation by one- and two-dimensional proton nuclear magnetic resonance and methylation analysis. Biochem. 23 (1984) 5628–5637.
Gilboa, 1986. *Biotechniques* 4, pp. 504–512.
Goochee, C. F., Gramer, M. J., Andersen, D. C., Baher, J. B. and Rasmussen, J. R.: The oligosaccharides of glycoproteins: bioprocess factors affecting oligosaccharide structure and their effect on glycoprotein properties. Biotechnol. 9 (1991) 1347–1355.
Good et al., 1992. *Transplant Procs* 24, pp. 558.
Hamadeh, R. M., Jarvis, G. A., Galili, U., Mandrell, R. E., Zhou, P. and Griffiss, J .M.: Human natural anti-Gal IgG regulates alternative complement pathway activation on bacterial surfaces. J.Clin.Invest. 89 (1992) 1223–1235.
Harlow and Lane, 1988. *Antibodies, A Laboratory Manual*, Cold Spring Harbor Laboratory, New York.
Hasty et al., 1991. *Mol Cell Bio* 11(11), pp. 5586–5591.
Hoshino, H., Tanaka, H., Miwa, M. and Okada, H.: Human T-cell leukemia virus is not lysed by human serum. Nature 310 (1984) 324–325.
Jasin and Berg, 1988. *Genes & Development* 2, pp. 1353–1363.
Jeannotte et al., 1991. *Mol Cell Bio* 11(11), pp. 5578–5585.
Jensen, F. C., Girardi, A. J., Gilden, R. V. and Koprowski, H.: Infection of human and simian tissue cultures with Rous sarcoma virus. Proc.Natl.Acad.Sci.USA 52 (1964) 53–57.
Jolly, D.: Viral vector systems for gene therapy. Cancer Gene Ther. 1 (1994) 51–64.
Joziasse, D. H., Shaper, J. H., Van den Eijnden, D. H., Van Tunen, A. J. and Shaper, N. L.: Bovine $\alpha$1-3-galactosyltransferase: isolation and characterization of a cDNA clone. J.Biol.Chem. 264 (1989) 14290–14297.
Kohn et al., 1989. *Cancer Invest* 7, pp. 179–192.
Korman et al., 1987. *Proc Natl Acad Sci, USA* 84, pp. 2150–2154.
Langer, 1990. *Science* 249, pp. 1527–1533.
Kornberg and Kornfeld 1985. *Ann. Rev. Biochem.* 54, 631–664.
Larsen et al., 1989. *Proc Natl Acad Sci, USA* 86, pp. 8227–8231.
Larsen, R. D., Ernst, L. K., Nair, R. P. and Lowe, J. B.: Molecular cloning, sequence, and expression of a human GDP-L-fucose:$\beta$-D-galactoside 2-$\alpha$-L-fucosyltransferase cDNA that can form the H blood group antigen. Proc.Natl.Acad.Sci.USA 87 (1990a) 6674–6678.
Larsen, R. D., Rivera-Marrero, C. A., Ernst, L. K., Cummings, R. D. and Lowe, J. B.: Frameshift and nonsense mutations in a human genomic sequence homologous to a murine UDP-Gal: $\beta$-D-Gal(1,4)-D-GlcNac$\alpha$(1, 3)-galactosyltransferase CDNA. J.Biol.Chem. 265 (1990b) 7055–7061.
Lehn, 1990. *Bone Marrow Transplantation* 5, pp. 287–293.
Liddell and Cryer, 1991. *A Practical Guide to Monoclonal Antibodies*, John Wiley & Sons, Chichester, West Sussex, England.
Lower, J., Davidson, E. A., Teich, N. M., Weiss, R. A., Joseph, A. P. and Kurth, R.: Hetrophil human antibodies recognize oncovirus envelope antigens: epidemiological parameters and immunological specificity of the reaction. Virol. 109 (1981) 409–417.
Mann et al., 1983. *Cell* 33, pp. 153–159.
Mansour et al., 1988. *Nature* 336, pp. 348–352.
Markowitz, D., Goff, S. and Band, A.: A safe packaging line for gene transfer: separating viral genes on two different plasmids. J.Virol. 62 (1988) 1120–1124.
Miller and Rosman, 1989. *Biotechnicues* 7, pp. 980–990.
Miller, 1992. *Nature* 357, pp. 455–460.
Miller, A. D. and Buttimore, C.: Redesign of retrovirus packaging cell lines to avoid recombination leading to helper virus production. Mol.Cell.Biol. 6 (1986) 2895–2902.
Miller, A. D. and Rosman, G. J.: Improved retroviral vectors for gene transfer and expression. Biotechniques 7 (1989) 980–990.
Morgenstern and Land, 1990. *Nucleic Acids Res* 18, pp. 3587–3596.
Mortensen et al., 1992. *Mol Cell Bio* 12(5), pp. 2391–2395.
Mulligan, 1983. In *Experimental Manipulation of Gene Expression* Inouye (ed), pp. 155–173.
Mulligan, 1993. *Science* 260, pp. 926–932.
Neethling, F. A., Koren, E., Ye, Y., Richards, S. V., Kujundzic, M., Oriol, R. and Cooper, D. K. C.: Protection of pig kidney (PK15) cells from the cytotoxic effect of anti-pig antibodies by a-galactosyl oligosaccharides. Transplantation 57 (1994) 959–963.

Pfizer, L. I., Cohen, G. H., Eisbernberg, R. J.: Effect of tunicamycin on herpes simplex virus glycoproteins and infectious virus production. J.Virology 34(1): 1980 142–53.

Rasheed, S., Gardner, M. B. and Chan, E.: Amphotropic host range of naturally occurring wild mouse leukemia viruses. J.Virol. 19 (1976) 13–18.

Rein, A.: Interference grouping of murine leukemia viruses: a distinct receptor for the MCF-recombinant viruses in mouse cells. Virol. 120 (1982) 251–257.

*Remington's Pharmaceutical Sciences*, 17th ed., 1985. Mack Publishing Company, Philadelphia, Pa. Chapters 37–39.

Repik, P. M., Strizki, J. M. and Galili, U.: Differential host-dependent expression of α-galactosyl epitopes on viral glycoproteins: a study of eastern equine encephalitis virus as a model. J.Gen.Virol. 75 (1994) 1177–1181.

Roitt et al., 1988. *Essential Immunology*, 6th Ed. Backwell Scientific Publications, Oxford, England.

Rother, R. P., Squinto, S. P., Mason, J. M. and Rollins, S. A.: Protection of retroviral vector particles in human blood through complement inhibition. Hum.Gene Ther. in press (1995) (in press)

Sambrook et al., 1989. *Molecular Cloning—A Laboratory Manual*, 2nd Ed. Cold Spring Harbor Laboratory, Cold Spring Harbor, N.Y.

Sandrin et al., 1993B. *Transplant Proc* 25, pp. 2917.

Sandrin, M. S., Vaughan, H. A., Dabkowski, P. L. and McKenzie, I. F. C.: Anti-pig IgM antibodies in human serum react predominantly with gal(α1-3)gal epitopes. Proc.Natl.Acad.Sci.USA 90 (1993) 11391–11395.

Sherwin, S. A., Benveniste, R. E. and Todaro, G. J.: Complement-mediated lysis of type-C virus: effect of primate and human sera on various retroviruses. Int.J-.Cancer 21 (1978) 6–11.

Snyder, H. W.,Jr. and Fleissner, E.: Specificity of human antibodies to oncovirus glycoproteins: recognition of antigen by natural antibodies directed against carbohydrate structures. Proc.Natl.Acad.Sci.USA 77 (1980) 1622–1626.

Spear, G. T., Jiang, H., Sullivan, B. L., Gewurz, H., Landay, A. L. and Lint, T. F.: Direct binding of complement component C1q to human immunodeficiency virus (HIV) and human T lymphotrophic virus-I (HTLV-I) coinfected cells. AIDS Res.Hum.Retroviruses 7 (1991) 579–585.

Takeuchi, Y., Cosset, F. C., Lachmann, P. J., Okada, H., Weiss, R. A. and Collins, M. K. L.: Type C retrovirus inactivation by human complement is determined by both the viral genome and the producer cell. J.Virol. 68 (1994) 8001–8007.

Teich, N. M., Weiss, R. A., Salahuddin, S. Z., Gallagher, R. E., Gillespie, D. H. and Gallo, R. C.: Infective transmission and characterization of a C-type virus released by cultured human myeloid leukemia cells. Nature 256 (1975) 551–555.

Thall and Galili, 1990. *Biochemistry* 29, pp. 3959.

Thiry, L., Cogniaux-Le Clerc, J., Content, J. and Tack, L.: Factors which influence inactivation of vesicular stomatitis virus by fresh human serum. Virol. 87 (1978) 384–393.

Thomas et al., 1986. *Cell* 44(3), pp. 419–428.

Thomas et al., 1987. *Cell* 51(3), pp. 503–512.

Tsichlis, P. N. and Lazo, P. A.: Virus-host interactions and the pathogenesis of murine and human oncogene retroviruses. Curr.Top.Microbiol.Immunol. 171 (1991) 95–171.

Tsichlis, P. N.: Oncogenesis by moloney murine leukemia virus. Anticancer Res. 7 (1987) 171–180.

Vaughan, H. A., Loveland, B. E. and Sandrin, M. S.: Galα(1,3)gal is the major xenoepitope expressed on pig endothelial cells recognized by naturally occurring cytotoxic human antibodies. Transplantation 58 (1994) 879–882.

Verma, 1990. *Scientific American* 263(5), pp. 68–84.

Warren et al., 1987. *Mol Cell Bio* 7, pp. 1326–1332.

Weatherall, 1991. *Nature* 349, pp. 275–276.

Welsh, Jr.,R. M.: Host cell modification of lymphocytic choriomeningitis virus and Newcastle disease virus altering viral inactivation by human complement. J.Immunol. 118 (1977) 348–354.

Welsh, R. M., Cooper, N. R., Jensen, F. C. and Oldstone, M. B. A.: Human serum lyses RNA tumour viruses. Nature 257 (1975) 612–614.

Welsh, R. M., Jensen, F. C., Cooper, N. R. and Oldstone, M. B. A.: Inactivation and lysis of oncornaviruses by human serum. Virol. 74 (1976) 432–440.

Widner and Brundin, 1988. *Brain Research Reviews* 13, pp. 287–324.

Wood, C., Kabat, E. A., Murphy, L. A. and Goldstein, I. J.: Immunochemical studies on the combining sites of two isolectins $A_4$ and $B_4$ isolated from *Bandeiraea simplicifolia*. Arch.Biochem.Biophys. 198 (1979) 1–9.

What is claimed is:

1. A method for protecting retroviral vector particles (RVVPs) from inactivation by human or Old World primate body fluids comprising treating said RVVPs with a glycolytic enzyme that is capable of reducing or removing galactose α (1,3) galactosyl epitope expression on said RVVP.

2. The method of claim 1 wherein said glycolytic enzyme is selected from the group consisting of alpha-galactosidase, beta-galactosidase, beta-N-acetylhexosaminidase, alpha-mannosidase, beta-mannosidase, endoglycosidase H, endoglycosidase F, and peptide-N-glycosidase F.

3. A retroviral vector particle produced by the method of claim 1.

4. A method for protecting retroviral vector particles (RVVPs) from inactivation by human or Old World primate body fluids comprising treating an RVVP producer cell line that expresses galactose α (1,3) galactosyl epitopes with a glycosylation inhibitor in an amount effective to reduce the expression of galactose α (1,3) galactosyl epitopes on RVVPs produced from said cell line.

5. The method of claim 4 wherein said glycosylation inhibitor is selected from the group consisting of deoxymannojirimycin, swainsonine, castanospermine, deoxynojirimycin, N-methyideoxynojirimycin, 2,5-dihydroxymethyl-3,4-dihydroxypyrrolidine,1,4-dideoxy-1, 4-imino-D-mannitol hydrochloride, australine, and bromoconduritol.

6. The method of claim 5 wherein said glycosylation inhibitor is castanospermine.

7. A retroviral vector particle produced by the method of claim 4.

8. A culture of retroviral vector particle (RVVP) producer cells derived from non-human, non-Old World primate cells wherein said cell culture has been incubated in a medium containing a glycosylation inhibitor in an amount effective to reduce the expression of galactose α (1,3) galactosyl epitopes on RVVPs produced from said cell culture.

9. The culture of claim 8 wherein said cells have been treated with a glycosylation inhibitor selected from the group consisting of deoxymennojirimycin, swainsonine, castanospermine, deoxynojirimycin, N-methyideoxynojirimycin, 2,5-dihydroxymethyl-3,4-dihydroxypyrrolidine,1,4-dideoxy-1,4-imino-D-mannitol hydrochloride, australine, and bromoconduritol.

10. The culture of claim 9 wherein said glycosylation inhibitor is castanospermine.

11. A retroviral vector particle isolated from the culture of claim 8.

* * * * *